US008609852B2

(12) United States Patent
Cosford et al.

(10) Patent No.: US 8,609,852 B2
(45) Date of Patent: Dec. 17, 2013

(54) THIAZOLYL MGLUR5 ANTAGONISTS AND METHODS FOR THEIR USE

(75) Inventors: Nicholas D. Cosford, San Diego, CA (US); Thomas J. Seiders, San Diego, CA (US); Joseph E. Payne, Oceanside, CA (US); Jeffrey R. Roppe, Temecula, CA (US); Dehua Huang, San Diego, CA (US); Nicholas D. Smith, San Diego, CA (US); Steve F. Poon, South Pasadena, CA (US); Chris King, Carlsbad, CA (US); Brian W. Eastman, San Diego, CA (US); Bowei Wang, San Diego, CA (US); Jeannie M. Arruda, LaJolla, CA (US); Jean-Michel Vernier, Laguna Niguel, CA (US); Xiumin Zhao, San Diego, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/558,537

(22) Filed: Jul. 26, 2012

(65) Prior Publication Data

US 2012/0289696 A1 Nov. 15, 2012

Related U.S. Application Data

(63) Continuation of application No. 13/016,304, filed on Jan. 28, 2011, now Pat. No. 8,242,143, which is a continuation of application No. 11/664,902, filed as application No. PCT/US2005/035921 on Oct. 6, 2005, now Pat. No. 7,879,882.

(60) Provisional application No. 60/616,805, filed on Oct. 7, 2004.

(51) Int. Cl.
*A61P 25/00* (2006.01)
*A61K 31/55* (2006.01)
*A61K 31/54* (2006.01)
*A61K 31/505* (2006.01)
*A61K 31/44* (2006.01)
*A61K 31/47* (2006.01)
*A61K 31/445* (2006.01)
*C07D 401/00* (2006.01)
*C07D 403/00* (2006.01)
*C07D 417/00* (2006.01)
*C07D 239/02* (2006.01)
*C07D 211/00* (2006.01)

(52) U.S. Cl.
USPC .............. 546/269.7; 514/217.04; 514/217.06; 514/227.8; 514/256; 514/274; 514/275; 514/300; 514/314; 514/318; 514/333; 514/342; 540/597; 540/601; 544/60; 544/316; 544/331; 544/333; 546/113; 546/167; 546/193; 546/256

(58) Field of Classification Search
USPC ............ 540/597, 601; 544/60, 316, 331, 333; 546/113, 167, 193, 256, 269.7
See application file for complete search history.

(56) References Cited

U.S. PATENT DOCUMENTS

| 6,774,138 | B2 | 8/2004 | Cosford et al. |
| 6,956,049 | B1 | 10/2005 | Cosford et al. |
| 7,365,074 | B2 | 4/2008 | Cosford et al. |
| 7,462,619 | B2 | 12/2008 | Cosford et al. |
| 7,879,882 | B2 | 2/2011 | Cosford et al. |
| 2007/0060618 | A1 | 3/2007 | Cosford et al. |

FOREIGN PATENT DOCUMENTS

| WO | WO0116121 | 3/2001 |
| WO | WO2004038374 | 5/2004 |

OTHER PUBLICATIONS

D. Alagille et al., "Synthesis and Receptor Assay of Aromatic-Ethynyl-Aromatic Derivatives with Potent mGluR5 Antagonist Activity", Bioorganic & Medicinal Chemistry, vol. 13, pp. 197-309, 2005.
J. Roppe et al., "5-[2-Methyl-1-1, 3-Thiazol-4-yl] Ethynl]-2,3'-Bipyridine: A Highly Potent, Orally Active Metabotropic Glutamate Subtype 5 (mGluR5) Receptor Antagonist with Anxiolytic Activity", Bioorganic & Medicinal Chemistry Letters, vol. 14, pp. 3993-3996, 2004.
J. Roppe et al., "Discovery of Novel Heteroarylazoles That Are Metabotropic Glutamate Subtype 5 Receptor Antagonists with Anxiolytic Activity", J. Med. Chem., vol. 47, pp. 4645-4648, 2004.
M. D. Green, et al., "Inhibition of human hepatic CYP isoforms by mGluR5 antagonists", Life Sciences, vol. 75, pp. 947-953, 2004.
Supplementary European Search Report for EP 05858618, dated Mar. 24, 2009.
Communication from EPO for EP 05858618, dated Jun. 2, 2009.
Submission by Applicant for EP 05858618, dated Mar. 25, 2010.
Communication from EPO for EP 05858618, dated Apr. 27, 2010.
Cosford et al., [3H]-Methoxymethyl-MTEP and [3H]-Methoxy-PEPy: Potent and Selective Radioligands for the Metabotropic Glutamate Subtype (mGlu5) Receptor, Bioorganic & Medicinal Chemistry Letters, vol. 13, No. 3, pp. 351-354, 2003.

*Primary Examiner* — Brenda Coleman
(74) *Attorney, Agent, or Firm* — J. Eric Thies; John C. Todaro

(57) ABSTRACT

The identification of a unique series of compounds which possesses special advantages in terms of drug-like properties due to their possessing advantageous properties in terms of potency and/or pharmacokinetic and/or selectivity and/or in vivo receptor occupancy properties. Specifically, the selection of a 1,3-thiazol-2-yl ring member linked by an ethynylene to the 3 position of a pyridyl ring or the 5 position of a pyrimidinyl ring, wherein the ring is substituted with selected substituents, results in a compound having superior drug-like properties. The invention includes pharmaceutically acceptable salt forms of these heterocyclic compounds, in particular chloride salts and trifluoroacetate salts.

2 Claims, No Drawings

THIAZOLYL MGLUR5 ANTAGONISTS AND METHODS FOR THEIR USE

CROSS REFERENCE TO RELATED APPLICATIONS

This application is a continuation of application Ser. No. 13/016,304, filed Jan. 28, 2011, now U.S. Pat. No. 8,242,143 which is a continuation of application Ser. No. 11/664,902, filed Apr. 6, 2007, now U.S. Pat. No. 7,879,882, issued on Feb. 1, 2011, which is a U.S. National Phase application under 35 U.S.C. §371 of PCT Application No. PCT/US2005/035921 filed Oct. 6, 2005, which claims priority under 35 U.S.C. §119 from U.S. Application No. 60/616,805, filed Jul. 10, 2004.

FIELD OF INVENTION

The present invention relates to the discovery of particular heterocyclic compounds, and further to particular salts of these heterocycles, possessing increased activity as mGluR5 antagonists. In addition, the present invention relates to therapeutic methods of use of these compounds for the treatment and prevention of various diseases and conditions.

BACKGROUND OF THE INVENTION

Unsaturated heterocylic compounds find a wide variety of uses. For example, compounds of this class find uses as modulators of physiological processes that are mediated by ligand-activated receptors. Receptors that are activated by ligands are located throughout the nervous, cardiac, renal, digestive and bronchial systems, among others. In the nervous system, for example, heterocyclic compounds are capable of functioning as agonists or antagonists of receptors for neurotransmitters, neurohormones and neuromodulators. Ligand-activated receptors have been identified in a wide variety of species, including humans, other mammals and vertebrates as well as in invertebrate species. Therefore, compounds of this class are also able to modulate receptor-mediated processes throughout phylogeny and find uses in a wide variety of applications, e.g., as pharmaceuticals, insecticides, fungicides and other uses.

Receptors activated by excitatory amino acids, such as the amino acid L-glutamic acid (glutamate), are a major excitatory neurotransmitter receptor class in the mammalian central nervous system. Anatomical, biochemical and electrophysiological analyses suggest that glutamatergic systems are involved in a broad array of neuronal processes, including fast excitatory synaptic transmission, regulation of neurotransmitter release, long-term potentiation, long-term depression, learning and memory, developmental synaptic plasticity, hypoxic-ischemic damage and neuronal cell death, epileptiform seizures, visual processing, as well as the pathogenesis of several neurodegenerative disorders. See generally, Nakanishi et al., Brain Research Reviews 26:230-235 (1998); Monaghan et al., Ann. Rev. Pharmacol. Toxicol. 29:365-402 (1980). This extensive repertoire of functions, especially those related to learning, neurotoxicity, and neuropathology, has stimulated recent attempts to describe and define the mechanisms through which glutamate exerts its effects.

Glutamate has been observed to mediate its effects through receptors that have been categorized into two main groups: ionotropic and metabotropic. Ionotropic glutamate receptors are generally divided into two classes: the N-methyl-D-aspartate (NMDA) and non-NMDA receptors. Both classes of receptors are linked to integral cation channels and share some amino acid sequence homology. GluR1-4 are termed AMPA (a-amino-3-hydroxy-5 methylisoxazole-4-propionic acid) receptors because AMPA preferentially activates receptors composed of these subunits, while GluRS-7 and KA1-2 are termed kainate receptors as these are preferentially sensitive to kainic acid. Thus, an "AMPA receptor" is a non-NMDA receptor that can be activated by AMPA. AMPA receptors include the GluR1-4 family, which form homo-oligomeric and hetero-oligomeric complexes which display different current-voltage relations and calcium permeability. Polypeptides encoded by GluR1-4 nucleic acid sequences can form functional ligand gated ion channels. An AMPA receptor includes a receptor having a GluR1, GluR2, GluR3 and/or GluR4 subunit. A NMDA receptor includes a receptor having NMDAR1, NMDAR2a, NMDAR2b, NMDAR2c, NMDAR2d and/or NMDAR3 subunits.

Metabotropic glutamate receptors are divided into three groups based on amino acid sequence homology, transduction mechanism and pharmacological properties, namely Group I, Group II and Group III. Each Group of receptors contains one or more types of receptors. For example, Group I includes metabotropic glutamate receptors 1 and 5 (mGluR1 and mGluR5), Group II includes metabotropic glutamate receptors 2 and 3 (mGluR2 and mGluR3) and Group III includes metabotropic glutamate receptors 4, 6, 7 and 8 (mGluR4, mGluR6, mGluR7 and mGluR8). Several subtypes of a particular mGluR type may exist. For example, subtypes of mGluR1 include mGluR1a, mGluR1b, mGluR1c and mGluR1d.

Anatomical studies demonstrate a broad and selective distribution of metabotropic glutamate receptors in the mammalian nervous system. For example, mGluR1 is expressed in the cerebellum, olfactory bulb, hippocampus, lateral septum, thalamus, globus pallidus, entopeduncular nucleus, ventral pallidum and substantia nigra (Petralia et al., (1997) J. Chem. Neuroanat., 13:77-93; Shigemoto et al., (1992) J. Comp. Neurol., 322:121-135). In contrast, mGluR5 is weakly expressed in the cerebellum, while higher levels of expression are found in the striatum and cortex (Romano et al., (1995) J. Comp. Neurol., 355:455-469). In the hippocampus, mGluR5 appears widely distributed and is diffusely expressed.

Metabotropic glutamate receptors are typically characterized by seven putative transmembrane domains, preceded by a large putative extracellular amino-terminal domain and followed by a large putative intracelluar carboxy-terminal domain. The receptors couple to G-proteins and activate certain second messengers depending on the receptor group. Thus, for example, Group I mGluR's activate phospholipase C. Activation of the receptors results in the hydrolysis of membrane phosphatidylinositol (4,5)-bisphosphate to diacylglycerol, which activates protein kinase C, and inositol trisphosphate, which in turn activates the inositol trisphosphate receptor to promote the release of 20 intracellular calcium.

A wide variety of heterocyclic compounds having activity as mGluR5 antagonists have been described in our International Publication No. WO 01/16121 and related national phase applications such as 09/387,073 (abandoned) and 10/217,800, issued as U.S. Pat. No. 6,774,138, for modulating the activity of the mGluR5 receptor and for use in the treatment of mGluR5 mediated conditions. Because of the physiological and pathological significance of excitatory amino acid receptors generally, and metabotropic glutamate receptors in particular, there is a need to identify ever more effective methods of modulating excitatory amino acid receptor-mediated processes, as well as more effective therapeutic methods of treatment and methods for prevention of diseases. There is thus a continuing need in the art to identify new and increasingly potent members of a compound class that can modulate excitatory amino acid receptors.

SUMMARY OF THE INVENTION

The identification of a series of compounds which falls within the scope of the group of compounds described and claimed in WO 01/16121 and in U.S. Pat. No. 6,744,138 but which is not specifically disclosed therein, which series of compounds possesses special advantages in terms of drug-like properties. That is, the compounds described herein show increased potential for use as drugs due to their possessing uniquely advantageous properties in terms of potency and/or selectivity and/or pharmacokinetic properties and/or in vivo receptor occupancy properties. Specifically, it has been discovered that the selection of a 1,3-thiazol-2-yl ring moiety linked by an ethynylene to the 3 position of a pyridyl ring or the 5 position of a pyrimidinyl ring, wherein the ring is substituted with selected substituents, results in a compound with superior drug-like properties. The invention also discloses pharmaceutically acceptable salt forms of these heterocyclic compounds, in particular chloride salts and trifluoroacetate salts.

The inventive compounds are useful for a wide variety of applications. For example these compounds can act to modulate physiological processes by functioning as antagonists of glutamate receptors in the nervous system. The inventive compounds may also act as insecticides and as fungicides. Pharmaceutical compositions containing invention compounds also have wide utility.

In accordance with the present invention, there are also provided methods of modulating the activity of excitatory amino acid receptors using a specifically defined class of heterocyclic compounds. In one embodiment, there are provided methods of modulating metabotropic glutamate receptors. The present invention also provides methods of treating disease using heterocyclic compounds. Diseases contemplated include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia and astrocytomas. The invention further discloses methods of preventing disease conditions related to diseases of the pulmonary system, diseases of the nervous system, diseases of the cardiovascular system, mental retardation (including mental retardation related to Fragile X syndrome), diseases of the gastrointestinal system such as gastroesophageal reflux disease and irritable bowel syndrome, diseases of the endocrine system, diseases of the exocrine system, diseases of the skin, cancer and diseases of the ophthalmic system.

DETAILED DESCRIPTION OF THE INVENTION

In accordance with the present invention, there are provided compounds of the formula:

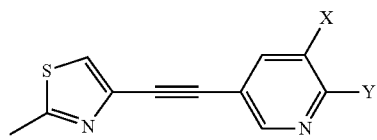

wherein X is H and Y is selected from:

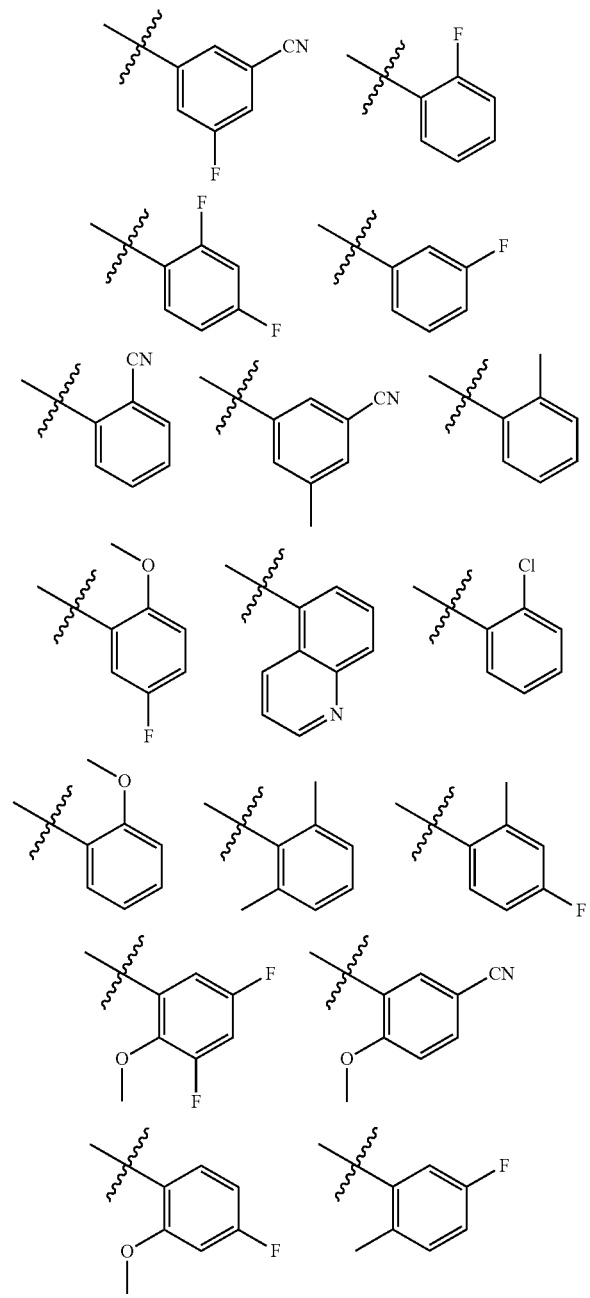

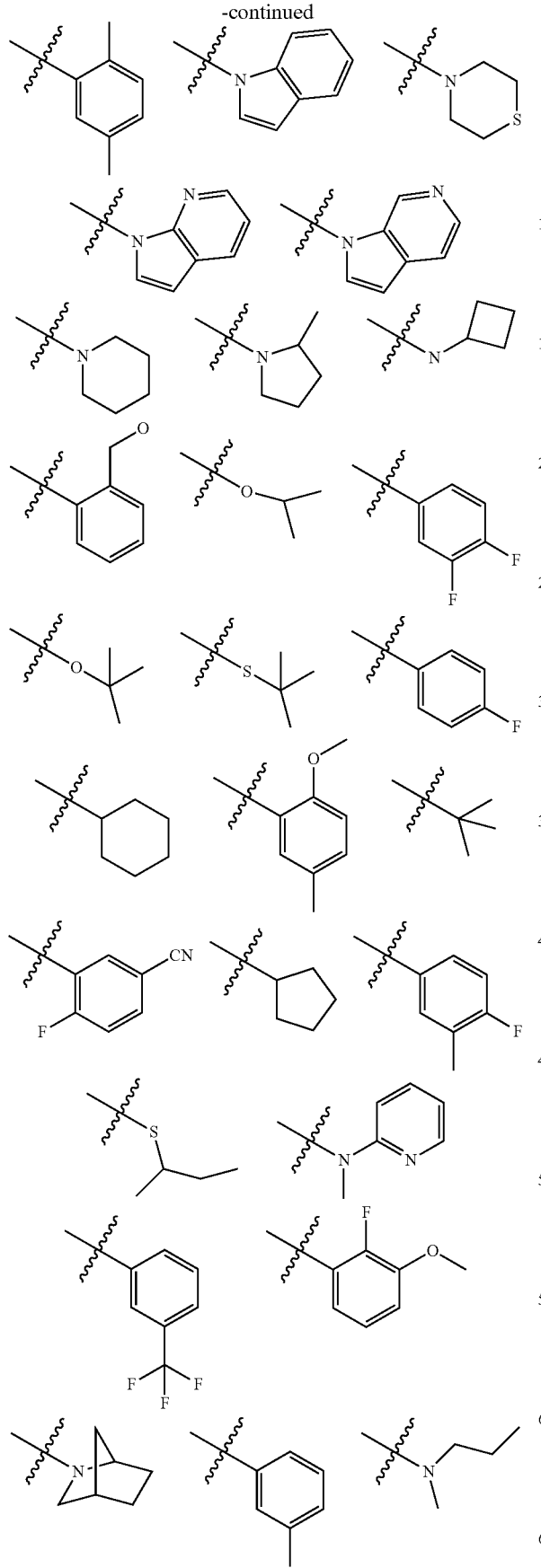
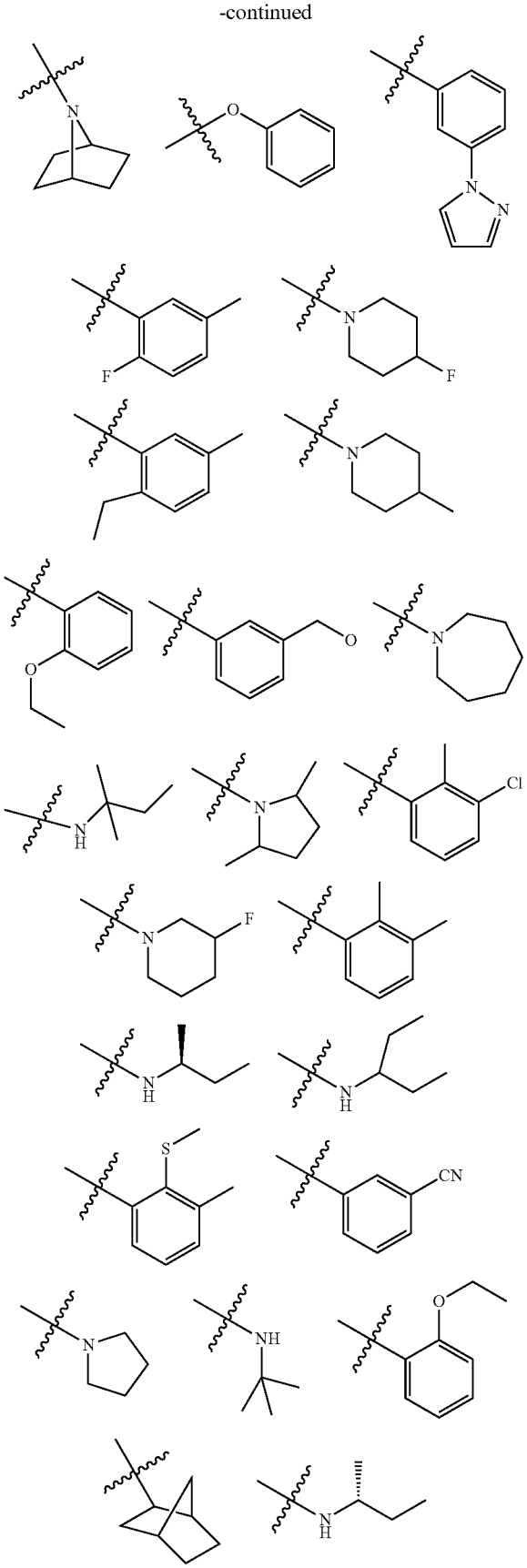

or wherein Y is H and X is selected from:

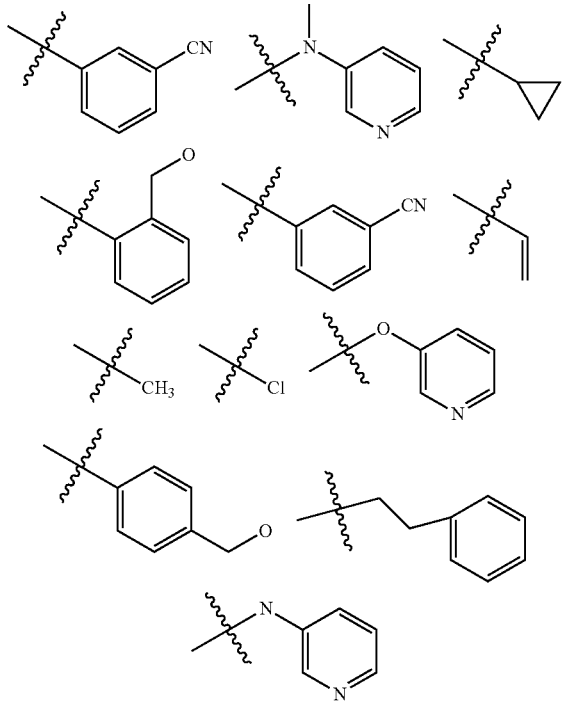

where said compound does not comprise radioisotopes, and pharmaceutically acceptable salts thereof.

Also in accordance with the present invention, there are provided compounds of the formula:

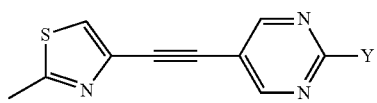

wherein Y is selected from:

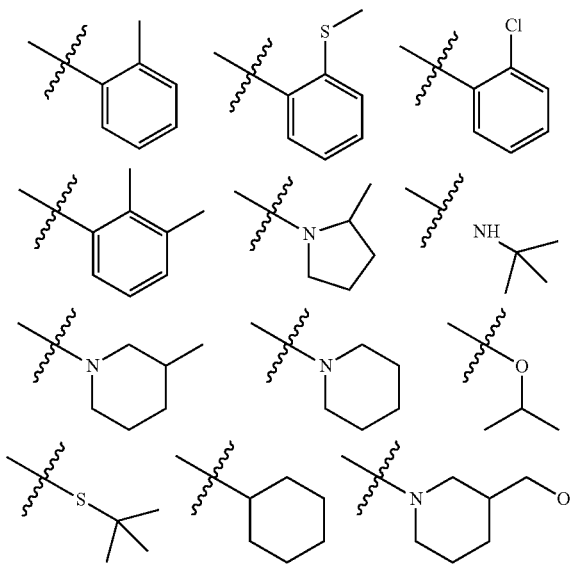

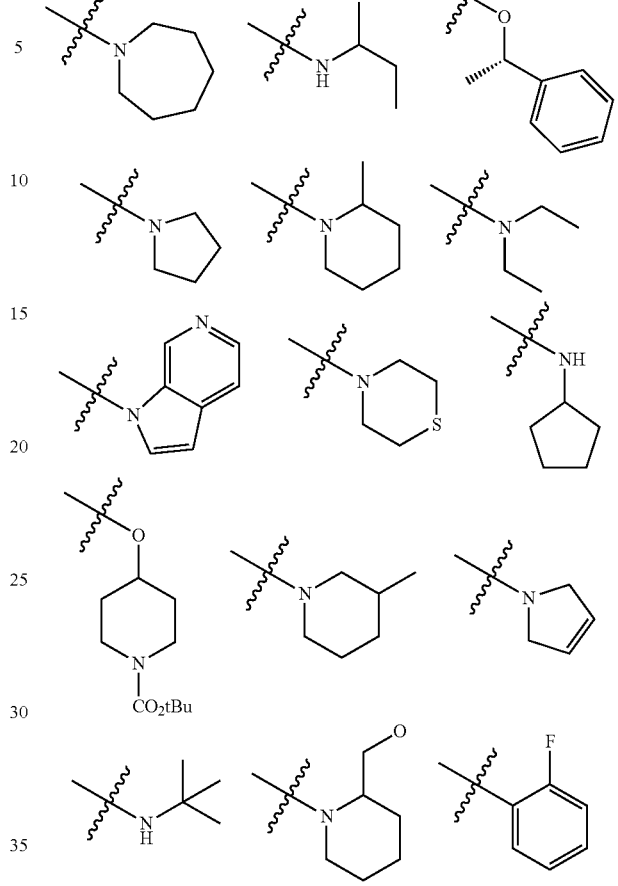

where said compound does not comprise radioisotopes, and pharmaceutically acceptable salts thereof.

As employed herein, "alkyl" refers to straight or branched chain alkyl radicals having in the range of about 1 up to 12 carbon atoms; "substituted alkyl" refers to alkyl radicals further bearing one or more substituents such as hydroxy, alkoxy, mercapto, aryl, heterocycle, halogen, trifluoromethyl, pentafluoroethyl, cyano, cyanomethyl, nitro, amino, amide, amidine, amido, carboxyl, carboxamide, carbamate, ester, sulfonyl, sulfonamide, and the like.

As employed herein, "halogen" refers to fluoride, chloride, bromide or iodide radicals.

Those of skill in the art recognize that invention compounds may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that invention compounds may exist in polymorphic forms wherein a compound is capable of crystallizing in different forms. Suitable methods for identifying and separating polymorphisms are known in the art.

In accordance with another embodiment of the present invention, there are provided pharmaceutical compositions comprising heterocyclic compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers) can be used in the manufacture of medicaments useful for the treatment of a variety of indications.

Pharmaceutically acceptable carriers contemplated for use in the practice of the present invention include carriers suitable for oral, sublingual intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non aqueous solutions, suspensions or emulsions, patches, and the like, is contemplated. Pharmaceutically acceptable carriers include glucose, lactose, gum acacia, gelatin, mannitol, starch paste, magnesium trisilicate, talc, corn starch, keratin, colloidal silica, potato starch, urea, dextrans, and the like.

Invention compounds can optionally be converted into non-toxic acid addition salts. Such salts are generally prepared by reacting the compounds of this invention with a suitable organic or inorganic acid Representative salts include hydrochloride, hydrobromide, sulfate, bisulfate, methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethanesulfonate, and the like. Salts can also be formed with inorganic acids such as sulfate, bisulfate, hemisulfate, hydrochloride, chlorate, perchlorate, hydrobromide, hydroiodide, and the like. Examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Such salts can readily be prepared employing methods well known in the art.

In accordance with another embodiment of the present invention, there are provided methods of modulating the activity of excitatory amino acid receptors, said method comprising contacting said receptors with at least one compound as described above. Thus, compounds contemplated for use in accordance with invention modulations methods include those having the structure A-L$^1$-B-L$^2$-Z (as described above and herein) or enantiomers, diastereomeric isomers or mixtures of any two or more thereof, or pharmaceutically acceptable salts thereof, in an amount sufficient to modulate the activity of said excitatory amino acid receptor.

As employed herein, "excitatory amino acid receptors" refers to a class of cell-surface receptors which are the major class of excitatory neurotransmitter receptors in the central nervous system. In addition, receptors of this class also mediate inhibitory responses. Excitatory amino acid receptors are membrane spanning proteins that mediate the stimulatory actions of the amino acid glutamate and possibly other endogenous acidic amino acids. Excitatory amino acids are crucial for fast and slow neurotransmission and they have been implicated in a variety of diseases including Alzheimer's disease, stroke, schizophrenia, head trauma, epilepsy, and the like. In addition, excitatory amino acids are integral to the processes of long-term potentiation and depression which are synaptic mechanisms underlying learning and memory. There are three main subtypes of excitatory amino acid receptors: (1) the metabotropic receptors; (2) the ionotropic NMDA receptors; and (3) the non-NMDA receptors, which include the AMPA receptors and kainate receptors.

As employed herein, the phrase "modulating the activity of refers to altered levels of activity so that the activity is different with the use of the invention method when compared to the activity without the use of the invention method. Modulating the activity of excitatory amino acid receptors includes the suppression or augmentation of the activity of receptors. Suppression of receptor activity may be accomplished by a variety of means, including blocking of a ligand binding site, biochemical and/or physico-chemical modification of a ligand binding site, binding of agonist recognition domains, preventing ligand-activated conformational changes in the receptor, preventing the activated receptor from stimulating second messengers such as G-proteins, and the like. Augmentation of receptor activity may be accomplished by a variety of means including, stabilization of a ligand binding site, biochemical and/or physico-chemical modification of a ligand binding site, binding of agonist recognition domains, promoting ligand-activated conformational changes in the receptor, and the like.

Excitatory amino acid receptor activity can be involved in numerous disease states. Therefore modulating the activity of receptors also refers to a variety of therapeutic applications, such as the treatment of cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia or astroytomas, and the like.

The compounds contemplated for use in accordance with of invention modulatory methods are especially useful for the treatment of mood disorders such as anxiety, depression, psychosis, drug withdrawal, tobacco withdrawal, memory loss, cognitive impairment, dementia, Alzheimer's disease, and the like; disorders of extrapyramidal motor function such as Parkinson's disease, progressive supramuscular palsy, Huntington's disease, Gilles de la Tourette syndrome, tardive dyskinesia, and the like.

Compounds contemplated for use in accordance with the invention are also especially useful for the treatment of pain disorders such as neuropathic pain, chronic pain, acute pain, painful diabetic neuropathy, post-herpetic neuralgia, cancer-associated pain, pain associated with chemotherapy, pain associated with spinal cord injury, pain associated with multiple sclerosis, causalgia and reflex sympathetic dystrophy, phantom pain, post-stroke (central) pain, pain associated with HIV or AIDS, trigeminal neuralgia, lower back pain, myofacial disorders, migraine, osteoarthritic pain, postoperative pain, dental pain, post-burn pain, pain associated with systemic lupus, entrapment neuropathies, painful polyneuropathies, ocular pain, pain associated with inflammation, pain due to tissue injury, and the like.

Moreover, compounds contemplated for use in accordance with the invention are especially useful for the treatment of cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia and astrocytomas. The invention further discloses methods of preventing disease conditions related to diseases of the pulmonary system, diseases of the nervous system, diseases of the cardiovascular system, mental retardation (including mental retardation related to Fragile X syndrome), diseases of the gastrointestinal system such as gastroesophageal reflux disease and irritable bowel syndrome, diseases of the endocrine system, diseases of the exocrine system, diseases of the skin, cancer and diseases of the ophthalmic system.

"Contacting" may include contacting in solution or in solid phase.

"Pharmaceutically acceptable salt" refers to a salt of the compound used for treatment which possesses the desired pharmacological activity and which is physiologically suitable. The salt can be formed with organic acids such as acetate, adipate, alginate, aspartate, benzoate, benzenesulfonate, butyrate, citrate, camphorate, camphorsulfonate, cyclopentanepropionate, digluconate, dodecylsulfate, ethanesulfonate, fumarate, glucoheptanoate, glycerophosphate, heptanoate, hexanoate, 2-hydroxyethanesulfonate, lactate, malate, maleate, methanesulfonate, 2-naphthalenesulfonate, nicotinate, oxalate, tartrate, toluenesulfonate, undecanoate, and the like. The salt can also be formed with inorganic acids such as sulfate, bisulfate, chlorate, perchlorate, hemisulfate, hydrochloride, hydrobromide, hydroiodide, and the like. In addition, the salt can be formed with a base salt, including 22 ammonium salts, alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like.

Salt forms of compounds herein find several advantages. Certain pharmaceutically acceptable salt forms of heterocyclic compounds described herein, achieve higher solubility as compared with nonsalt forms. In addition, certain salt forms are more compatible with pharmaceutical uses. For example, the hydrochloric acid salt of 2-(phenylethynl)-1,3-thiazole is an oil while the toluene sulfonic acid salt form of 2-(phenylethynl)-1,3-thiazole is a solid that is soluble in aqueous medium. Characteristics of salt forms of compounds depend on the characteristics of the compound so treated, and on the particular salt employed.

In accordance with another embodiment of the invention, there are provided methods of modulating the activity of metabotropic glutamate receptors, said method comprising contacting metabotropic glutamate receptors with a concentration of a heterocylic compound as described above in accordance with invention methods for modulating the activity of excitatory amino acid receptors, sufficient to modulate the activity of said metabotropic glutamate receptors.

As used herein, the phrase "metabotropic glutamate receptor" refers to a class of cell-surface receptors which participates in the G-protein-coupled response of cells to glutamatergic ligands. Three groups of metabotropic glutamate receptors, identified on the basis of amino acid sequence homology, transduction mechanism and binding selectivity are presently known and each group contains one or more types of receptors. For example, Group I includes metabotropic glutamate receptors 1 and 5 (mGluR1 and mGluR5), Group II includes metabotropic glutamate receptors 2 and 3 (mGluR2 and mGluR3) and Group III includes metabotropic glutamate receptors 4, 6, 7 and 8 (mGluR4, mGluR6, mGluR7 and mGluR8). Several subtypes of each mGluR type may be found; for example, subtypes of mGluR1 include mGluR1a, mGluR1b and mGluR1c.

In accordance with another embodiment of the invention, there are provided methods of treating a wide variety of disease conditions, said method comprising administering to a patient having a disease condition a therapeutically effective amount of at least one of the heterocyclic compounds described above in accordance with invention methods for modulating the activity of excitatory amino acid receptors.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

Disease conditions contemplated for treatment in accordance with the invention include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia, astrocytomas, and the like.

Disease conditions contemplated for treatment in accordance with the present invention further include diseases of the pulmonary system, diseases of the nervous system, diseases of the cardiovascular system, diseases of the gastrointestinal system, diseases of the endocrine system, diseases of the exocrine system, diseases of the skin, cancer, diseases of the ophthalmic system, and the like.

As used herein, "administering" refers to means for providing heterocyclic compounds and/or salts thereof, as described herein, to a patient; using oral, sublingual intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

For purposes of oral administration, tablets, capsules, troches, aqueous or oily suspensions, dispersible powders or granules, emulsions, hard or soft capsules, or syrups, elixirs and lozenges containing various excipients such as calcium carbonate, lactose, calcium phosphate, sodium phosphate, and the like may be employed along with various granulating and disintegrating agents such as corn starch, potato starch, alginic acid, and the like, together with binding agents such as gum tragacanth, corn starch, gelatin, acacia, and the like. Lubricating agents such as magnesium stearate, stearic acid, talc, and the like may also be added. Preparations intended for oral use may be prepared according to any methods known to the art for the manufacture of pharmaceutical preparations and such preparations may contain one or more agents selected from the group consisting of a sweetening agent such as sucrose, lactose, saccharin, and the lake, flavoring agents such as peppermint, oil of wintergreen, and the like, coloring agents and preserving agents in order to provide pharmaceutically palatable preparations.

Preparations for oral use may also contain suitable carriers include emulsions, solutions, suspensions, syrups, and the like, optionally containing additives such as wetting agents, emulsifying and suspending 24 agents, sweetening, flavoring and perfuming agents, and the like. Tablets may be uncoated or they may be coated by known techniques to delay disintegration and absorption in the gastrointestinal tract and thereby provide a sustained action over a longer period of time.

For the preparation of fluids for parenteral administration, suitable carriers include sterile aqueous or non-aqueous solutions, suspensions, or emulsions. For parenteral administration, solutions for the practice of the invention may comprise sterile aqueous saline solutions, or the corresponding water soluble pharmaceutically acceptable metal salts, as previously described. For parenteral administration, solutions of the compounds used in the practice of the invention may also comprise non-aqueous solutions, suspensions, emulsions, and the like. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Aqueous solutions may also be suitable for intravenous, intramuscular, intrathecal, subcutaneous, and intraperitoneal injection. The sterile aqueous media employed are all readily obtainable by standard techniques well known to those skilled in the art. They may be sterilized, for example, by filtration through a bacteria-retaining filter, by incorporating sterilizing agents into the compositions, by irradiating the compositions, by heating the compositions, and the like. They can also be manufactured in the form of sterile water, or some other sterile medium capable of injection immediately before use.

Compounds contemplated for use in accordance with the present invention may also be administered in the form of suppositories for rectal or vaginal administration. These compositions may be prepared by mixing the drug with a suitable non-irritating excipient, such as cocoa butter, synthetic glyceride esters of polyethylene glycols, and the like, such materials being solid at ambient temperatures but liquify and/or dissolve in internal cavities to release the drug.

The preferred therapeutic compositions for inocula and dosage will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound without the weight of carrier (when carrier is used).

The route of delivery of compounds and compositions used for the practice of the invention is determined by the disease and the site where treatment is required. Since the pharmacokinetics and pharmacodynamics of compounds and compositions described herein will vary somewhat, the most preferred method for achieving a therapeutic concentration in a tissue is to gradually escalate the dosage and monitor the clinical effects. The initial dose, for such an escalating dosage regimen of therapy, will depend upon the route of administration.

In accordance with invention methods, the medicinal preparation can be introduced parenterally, by dermal application, and the like, in any medicinal form or composition. It is used as a solitary agent of medication or in combination with other medicinal preparations. Single and multiple therapeutic dosage regimens may prove useful in therapeutic protocols.

As employed herein, the phrase "a therapeutically effective amount", when used in reference to invention methods employing heterocyclic compounds and pharmaceutically acceptable salts thereof, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, —the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being preferred.

In still another embodiment of the invention, there are provided methods for preventing disease conditions in a subject at risk thereof, said method comprising administering to said subject a therapeutically effective amount of at least one of the heterocyclic compounds described above in accordance with invention methods for modulating the activity of excitatory amino acid receptors.

As used herein, the phrase "preventing disease conditions" refers to preventing a disease, disorder or condition from occurring in a subject who may be at risk for the disease, but has not yet been diagnosed as having the disease. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general health, occupation, exposure to environmental conditions, marital status, and the like, of the subject.

Those of skill in the art can readily identify a variety of assays that can be used to assess the activity of excitatory amino acid receptors. For receptor species that activate a second messenger pathway, assays that measure receptor-activated changes in intracellular second messengers can be employed to monitor receptor activity. For example, inhibition of G-protein-coupled metabotropic glutamate receptors using a radioligand binding assay. (See Example 109.)

Similarly, activation of excitatory amino acid receptors that leads to the release of intracellular calcium or changes in intracellular calcium concentration can also be used to assess excitatory amino acid receptor activity. Methods of detection of transient increases in intracellular calcium concentration are well known in the art. (See e.g., Ito et al., J. Neurochem. 56:531-540 (1991) and Example 108). G-protein coupled receptors are also coupled to other second messenger systems such as phosphatidylinositol hydrolysis (see, e.g., Berridge et al., (1982) Biochem. J. 206: 587-5950; and Nakajima et al., J. Biol. Chem. 267:2437-2442 (1992) and Example 110).

The following examples are intended to illustrate but not to limit the invention in any manner, shape, or form, either explicitly or implicitly. While they are typical of those that might be used, other procedures, methodologies, or techniques known to those skill in the art may alternatively be used.

Intermediate 1

2-chloro-5-[(2-methyl-1,3-thiazol-4-yl)ethynyl]pyridine

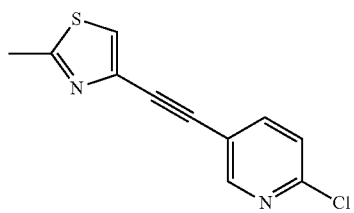

2-Chloro-5-iodopyridine (40 mmol, 10.0 g), 2-methyl-4-[(trimethylsilyl)ethynyl]-1,3-thiazole (40 mmol, 7.8 g), dichlorobis(triphenylphosphine)palladium(II) (2 mmol, 1.4 g), copper(I) iodide (4 mmol, 760 mg) and triethylamine (200 mmol, 28 mL) were added to deoxygenated DMF (200 mL) at room temperature. The reaction was then warmed to 60° C. and tetrabutylammonium fluoride (40 mmol, 40 mL of 1.0 M solution in THF) was added dropwise via syringe. Stirring continued for 2.5 hrs and the reaction contents were then poured in to a separatory funnel and partitioned with 1:1 hexanes:EtOAc (1000 mL) and water (500 mL). The organic layer was then washed with 5 portions of 5% NaCl (250 mL each). The combined aqueous layers were back-extracted with 1:1 hexanes:EtOAc (500 mL). The combined organic layers were dried over MgSO$_4$, filtered, and concentrated in vacuo. The crude residue was chromatographed on SiO$_2$, eluting with 1:1 EtOAc:hexanes to afford 2-chloro-5-[(2-methyl-1,3-thiazol-4-yl)ethynyl]pyridine as a tan solid. $^1$H-NMR (CDCl$_3$, 300 MHz) δ 8.57 (s, 1H), 7.77 (d, 1H), 7.45 (s, 1H), 7.32 (d, 1H), 2.75 (s, 3H). MS (ESI) 235.2 (M+H$^+$).

Intermediate 2

2-chloro-5-[(2-methyl-1,3-thiazol-4-yl)ethynyl]pyrimidine

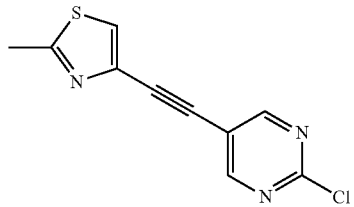

2-Chloro-5-bromopyrimidine (5.0 g, 26 mmol), 2-methyl-4-ethynyl-1,3-thiazole (3.2 g, 26 mmol), tetrakis(triphenylphosphine)palladium(0) (0.6 g, 0.5 mmol), copper(I) iodide (0.1 g, 0.5 mmol) and triethylamine (13 g, 130 mmol) were added to deoxygenated toluene (50 mL) at room temperature. The reaction was then warmed to 60° C. Stirring continued for 2.5 hrs and the reaction contents were then poured in to a separatory funnel and partitioned with EtOAc (100 mL) and water (100 mL). The organic layer was then washed with water twice (250 mL each). The organic layer were dried over MgSO$_4$, filtered, and concentrated in vacuo. The crude residue was chromatographed on SiO$_2$, eluting with 1:1 EtOAc:hexanes to afford 2-chloro-5-[(2-methyl-1,3-thiazol-4-yl)ethynyl]pyrimidine as a tan solid. $^1$H-NMR (CDCl$_3$, 300 MHz) δ 8.78 (s, 2H), 7.52 (s, 1H), 2.78 (s, 3H).

Example 1

3-fluoro-5-{5-[(2-methyl-1,3-thiazol-4-yl)ethynyl]pyridin-2-yl}benzonitrile

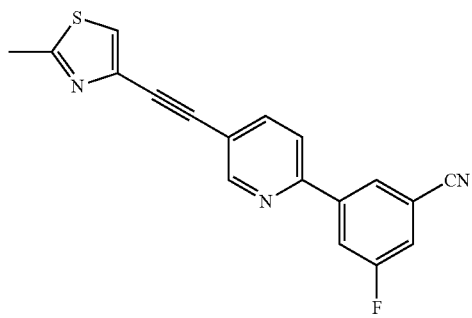 [SMILES: Cc1nc(C#Cc2ccc(-c3cc(F)cc(C#N)c3)nc2)cs1]

Step 1: 3-fluoro-5-(4,4,5,5-tetramethyl-1,3,2-dioxaborolan-2-yl)benzonitrile

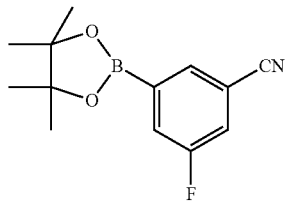 [SMILES: CC1(C)OB(c2cc(F)cc(C#N)c2)OC1(C)C]

3-Bromo-5-fluorobenzonitrile (30.0 mmol, 9.23 g), bis(pinacolato)diboron (30.0 mmol, 7.62 g), PdCl$_2$(dppf)$_2$ (1:1 complex with dichloromethane, 1.2 mmol, 980 mg), and potassium acetate (105 mmol, 10.3 g) were combined in deoxygenated dioxane (150 mL) and heated at 80° C. for 4 hrs, at which time the reaction was determined to be complete by GC/MS analysis. The reaction was cooled to room temperature, and poured in to a separatory funnel containing EtOAc (300 mL) and water (200 mL). The aqueous layer was back extracted with EtOAc (75 mL), and the combined organic layers were dried over MgSO$_4$, filtered, and concentrated in vacuo. The crude residue was carried on to the next step with out further purification or characterization.

Step 2: 3-fluoro-5-{5-[(2-methyl-1,3-thiazol-4-yl)ethynyl]pyridin-2-yl}benzonitrile

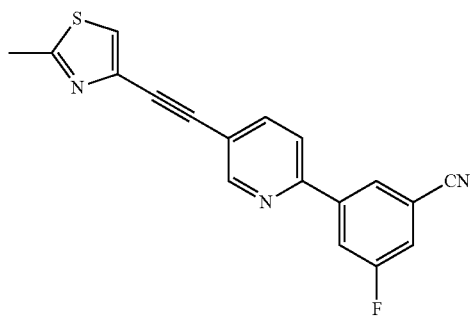 [SMILES: Cc1nc(C#Cc2ccc(-c3cc(F)cc(C#N)c3)nc2)cs1]

2-chloro-5-[(2-methyl-1,3-thiazol-4-yl)ethynyl]pyridine (30 mmol, 7.02 g) and 3-fluoro-5-(4,4,5,5-tetramethyl-1,3,2-dioxaborolan-2-yl)benzonitrile (30 mmol, crude material, above procedure), dichlorobis(triphenylphosphine)palladium(II) (1.5 mmol, 1.05 g), and potassium carbonate (120 mmol, 16.6 g) were added to deoxygenated DME:water (1:1, 300 mL) at room temperature. The reaction was warmed to 80° C. and stirred overnight under nitrogen, then partitioned in a separatory funnel with EtOAc (500 mL) and water (300 mL). The organic layer was washed with one additional portion of water (100 mL) and the combined aqueous layers back extracted with EtOAc (100 mL). The combined organic layers were dried over MgSO$_4$, filtered, and concentrated in vacuo. The crude residue was chromatographed on SiO$_2$, eluting with 30% EtOAc in hexanes, to afford the title compound as a tan solid. $^1$H-NMR (CDCl$_3$, 500 MHz) δ 8.89 (m, 1H), 8.17 (dd, 1H), 8.04 (m, 1H), 7.98 (dd, 1H), 7.75 (d, 1H), 7.50 (s, 1H), 7.42 (m, 1H), 2.79 (s, 3H). MS (ESI) 320.0 (M+H$^+$).

3-fluoro-5-{5-[(2-methyl-1,3-thiazol-4-yl)ethynyl]pyridin-2-yl}benzonitrile was dissolved in methylene chloride and an equal molar amount of HCl in ether was added dropwise. The solvent was evaporated in vaccuo to yield an off white solid. MS (ESI) 320.0 (M+H$^+$).

Example 2

2-(2-fluorophenyl)-5-[(2-methyl-1,3-thiazol-4-yl)ethynyl]pyridine

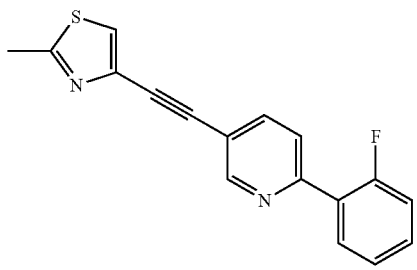 [SMILES: Cc1nc(C#Cc2ccc(-c3ccccc3F)nc2)cs1]

2-chloro-5-[(2-methyl-1,3-thiazol-4-yl)ethynyl]pyridine (0.43 mmol, 100 mg), 2-fluorophenylboronic acid (0.47 mmol, 66 mg), dichlorobis(triphenylphosphine)palladium(II) (0.03 mmol, 18 mg), and potassium carbonate (1.72 mmol, 238 mg) were added to deoxygenated DME:water (1:1, 3 mL) at room temperature. The reaction was heated for 5 min at 150° C. via microwave irradiation, then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 10 to 40% EtOAc gradient in hexanes, to afford the title compound as a tan solid, which was dissolved in ether and precipitated as the hydrochloride salt with 1M HCl in ether. $^1$H-NMR (CD$_3$OD, 500 MHz) δ 9.13 (s, 1H), 8.69 (d, 1H), 8.30 (d, 1H), 7.98 (s, 1H), 7.84 (dd, 1H), 7.70 (m, 1H), 7.42-7.53 (m, 2H), 2.83 (s, 3H). MS (ESI) 295.13 (M+H$^+$).

Example 3

2-(3-fluorophenyl)-5-[(2-methyl-1,3-thiazol-4-yl)ethynyl]pyridine

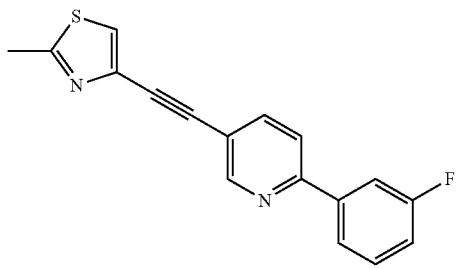 [SMILES: Cc1nc(C#Cc2ccc(-c3cccc(F)c3)nc2)cs1]

2-chloro-5-[(2-methyl-1,3-thiazol-4-yl)ethynyl]pyridine (0.43 mmol, 100 mg), 3-fluorophenylboronic acid (0.47 mmol, 66 mg), dichlorobis(triphenylphosphine)palladium(II) (0.03 mmol, 18 mg), and potassium carbonate (1.72 mmol, 238 mg) were added to deoxygenated DME:water (1:1, 3 mL) at room temperature. The reaction was heated for 5 min at 150° C. via microwave irradiation, then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 10 to 40% EtOAc gradient in hexanes, to afford the title compound as a tan solid, which was dissolved in ether and precipitated as the hydrochloride salt with 1M HCl in ether. $^1$H-NMR (CD$_3$OD, 500 MHz) δ 8.99 (s, 1H), 8.58 (d, 1H), 8.28 (d, 1H), 7.95 (s, 1H), 7.74 (m, 2H), 7.60 (m, 1H), 7.38 (m, 1H), 2.73 (s, 3H). MS (ESI) 295.13 (M+H$^+$).

Example 4

2-{5-[(2-methyl-1,3-thiazol-4-yl)ethynyl]pyridin-2-yl}benzonitrile

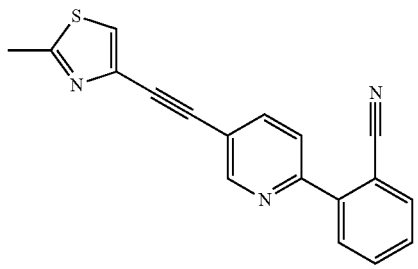 [SMILES: Cc1nc(C#Cc2ccc(-c3ccccc3C#N)nc2)cs1]

2-chloro-5-[(2-methyl-1,3-thiazol-4-yl)ethynyl]pyridine (1.0 mmol, 234 mg), 2-cyanophenylboronic acid (1.2 mmol, 176 mg), dichlorobis(triphenylphosphine)palladium(II) (0.05 mmol, 35 mg), and potassium carbonate (3.5 mmol, 500 mg) were added to deoxygenated DME:water (1:1, 5 mL) at room temperature. The reaction was heated for 5 min at 150° C. via microwave irradiation, then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 0% to 60% EtOAc gradient in hexanes, to afford the title compound as a white solid, which was dissolved in ether and precipitated as the hydrochloride salt with 1M HCl in ether. MS (ESI) 301.4 (M+H$^+$).

Example 5

2-(2-methylphenyl)-5-[(2-methyl-1,3-thiazol-4-yl)ethynyl]pyridine

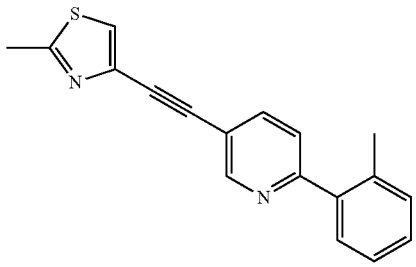

2-chloro-5-[(2-methyl-1,3-thiazol-4-yl)ethynyl]pyridine (1.0 mmol, 234 mg), 2-methylphenylboronic acid (2.0 mmol, 272 mg), dichlorobis(triphenylphosphine)palladium(II) (0.05 mmol, 35 mg), and potassium carbonate (3.5 mmol, 500 mg) were added to deoxygenated DME:water (1:1, 5 mL) at room temperature. The reaction was heated for 18 h at 80° C., then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 0% to 60% EtOAc gradient in hexanes, to afford the title compound as a tan solid, which was dissolved in ether and precipitated as the hydrochloride salt with 1M HCl in ether. $^1$H-NMR (CD$_3$OD, 500 MHz) δ 9.14 (s, 1H), 8.76 (d, 1H), 8.18 (d, 1H), 8.03 (s, 1H), 7.44-7.61 (m, 4H), 2.76 (s, 3H), 2.26 (s, 3H). MS (ESI) 291.2 (M+H$^+$).

Example 6

2-(5-fluoro-2-methoxyphenyl)-5-[(2-methyl-1,3-thiazol-4-yl)ethynyl]pyridine

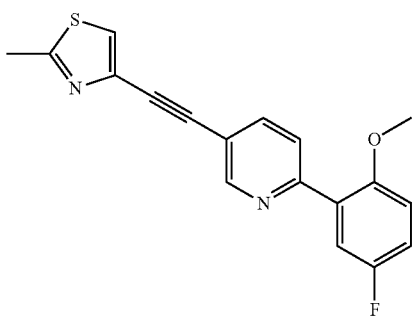

2-chloro-5-[(2-methyl-1,3-thiazol-4-yl)ethynyl]pyridine (1.0 mmol, 234 mg), 2-methoxy-5-fluorophenylboronic acid (2.0 mmol, 340 mg), dichlorobis(triphenylphosphine)palladium(II) (0.05 mmol, 35 mg), and potassium carbonate (3.5 mmol, 500 mg) were added to deoxygenated DME:water (1:1, 5 mL) at room temperature. The reaction was heated for 18 h at 80° C., then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 0% to 60% EtOAc gradient in hexanes, to afford the title compound as a tan solid, which was dissolved in ether and precipitated as the hydrochloride salt with 1M HCl in ether. $^1$H-NMR (CD$_3$OD, 500 MHz) δ 9.08 (s, 1H), 8.73 (d, 1H), 8.34 (d, 1H), 8.03 (s, 1H), 7.58 (dd, 1H), 7.45 (m, 1H), 7.33 (m, 1H), 3.97 (s, 3H), 2.77 (s, 3H). MS (ESI) 325.4 (M+H$^+$).

Example 7

2-(2-chlorophenyl)-5-[(2-methyl-1,3-thiazol-4-yl)ethynyl]pyridine

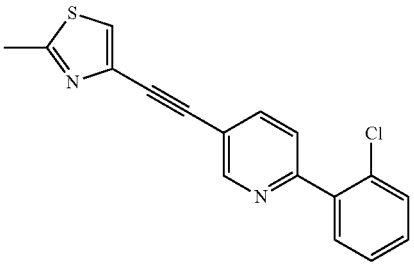 [SMILES: Cc1nc(C#Cc2ccc(-c3ccccc3Cl)nc2)cs1]

2-chloro-5-[(2-methyl-1,3-thiazol-4-yl)ethynyl]pyridine (1.0 mmol, 234 mg), 2-methoxy-5-fluorophenylboronic acid (2.0 mmol, 312 mg), dichlorobis(triphenylphosphine)palladium(II) (0.05 mmol, 35 mg), and potassium carbonate (3.5 mmol, 500 mg) were added to deoxygenated DME:water (1:1, 5 mL) at room temperature. The reaction was heated for 18 h at 80° C., then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 0% to 60% EtOAc gradient in hexanes, to afford the title compound as a tan solid, which was dissolved in ether and precipitated as the hydrochloride salt with 1M HCl in ether. $^1$H-NMR (CD$_3$OD, 500 MHz) δ 9.15 (s, 1H), 8.73 (d, 1H), 8.20 (d, 1H), 7.97 (s, 1H), 7.57-7.69 (m, 3H), 7.59 (m, 1H), 2.77 (s, 3H). MS (ESI) 310.9 (M+H$^+$).

Example 8

2-(2-methoxyphenyl)-5-[(2-methyl-1,3-thiazol-4-yl)ethynyl]pyridine

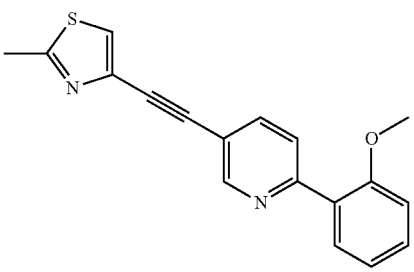

2-chloro-5-[(2-methyl-1,3-thiazol-4-yl)ethynyl]pyridine (1.0 mmol, 234 mg), 2-methoxyphenylboronic acid (2.0 mmol, 304 mg), dichlorobis(triphenylphosphine)palladium (II) (0.05 mmol, 35 mg), and potassium carbonate (3.5 mmol, 500 mg) were added to deoxygenated DME:water (1:1, 5 mL) at room temperature. The reaction was heated for 18 h at 80° C., then partitioned in a separatory funnel with EtOAc (100 mL) and water (30 mL). The organic layer was washed with one additional portion of water (20 mL) and the combined aqueous layers back extracted with EtOAc (50 mL). The combined organic layers were dried over MgSO$_4$, filtered, and concentrated in vacuo. The crude residue was chromatographed on SiO$_2$, eluting with a 0% to 60% EtOAc gradient in hexanes, to afford the title compound as a pale yellow solid, which was dissolved in ether and precipitated as the hydrochloride salt with 1M HCl in ether. $^1$H-NMR (CD$_3$OD, 500 MHz) δ 9.02 (s, 1H), 8.73 (d, 1H), 8.34 (d, 1H), 7.97 (s, 1H), 7.68-7.77 (m, 2H), 7.32 (d, 1H), 7.24 (dd, 1H), 3.99 (s, 3H), 2.77 (s, 3H). MS (ESI) 307.2 (M+H$^+$).

The following compounds were prepared using a similar method as described in Example 8 for 2-(2-methoxyphenyl)-5-[(2-methyl-1,3-thiazol-4-yl)ethynyl]pyridine:

Example 9

2-(4-fluoro-2-methylphenyl)-5-[(2-methyl-1,3-thiazol-4-yl)ethynyl]pyridinium trifluoroacetate

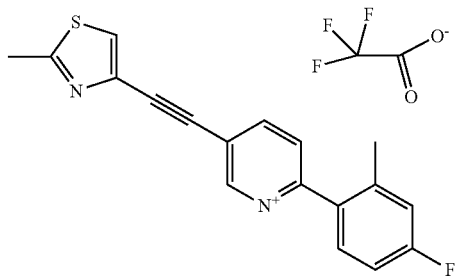 [SMILES: Cc1nc(C#Cc2ccc(-c3ccc(F)cc3C)[nH+]c2)cs1 ; O=C([O-])C(F)(F)F]

MS (ESI) 310 (M+H$^+$).

Example 10

2-(3,5-difluoro-2-methoxyphenyl)-5-[(2-methyl-1,3-thiazol-4-yl)ethynyl]pyridinium trifluoroacetate

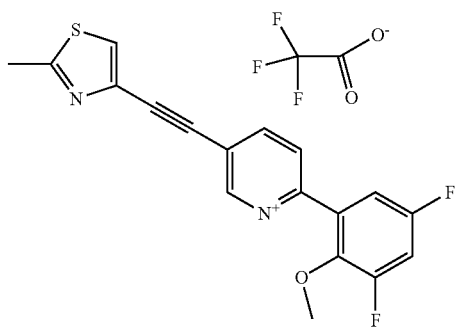 [SMILES: COc1c(F)cc(F)cc1-c1ccc(C#Cc2csc(C)n2)c[nH+]1 ; O=C([O-])C(F)(F)F]

$^1$H-NMR (CDCl$_3$, 500 MHz). 8.71 (m, 1H), 8.02 (m, 1H), 7.98 (m, 1H), 7.78 (m, 1H), 7.39 (m, 1H), 7.12 (m, 1H), 3.85 (s, 3H), 2.80 (s, 3H). MS (ESI) 343 (M+H$^+$).

Example 11

2-(4-fluoro-2-methoxyphenyl)-5-[(2-methyl-1,3-thiazol-4-yl)ethynyl]pyridinium trifluoroacetate

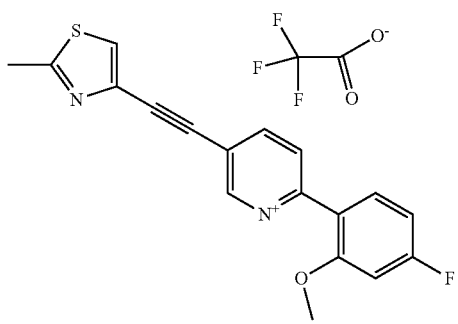 [SMILES: COc1cc(F)ccc1-c1ccc(C#Cc2csc(C)n2)c[nH+]1 ; O=C([O-])C(F)(F)F]

MS (ESI) 326 (M+H$^+$).

Example 12

2-(5-fluoro-2-methylphenyl)-5-[(2-methyl-1,3-thiazol-4-yl)ethynyl]pyridinium trifluoroacetate

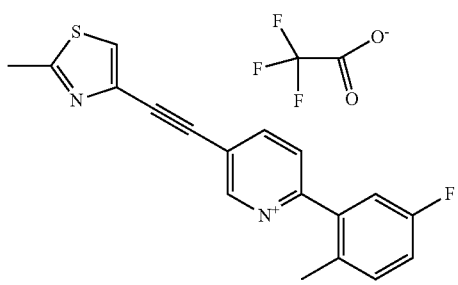 [SMILES: Cc1nc(C#Cc2ccc(-c3cc(F)ccc3C)[nH+]c2)cs1 ; O=C([O-])C(F)(F)F]

MS (ESI) 309 (M+H$^+$).

Example 13

2-(2-methylphenyl)-5-[(2-methyl-1,3-thiazol-4-yl)ethynyl]pyrimidine

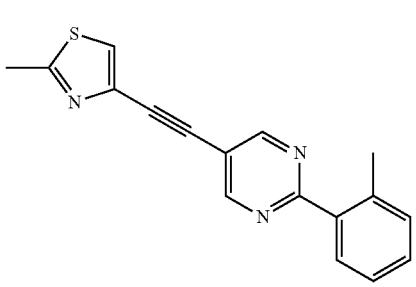 [SMILES: Cc1nc(C#Cc2cnc(-c3ccccc3C)nc2)cs1]

2-chloro-5-[(2-methyl-1,3-thiazol-4-yl)ethynyl]pyrimidine (200 mg, 0.85 mmol), 2-methylphenylboronic acid (250 mg, 1.7 mmol), Pd₂dba₃ (20 mg, 0.021 mmol), [2'-(dicyclohexylphosphino)biphenyl-2-yl]dimethylamine (15 mg, 0.038 mmol) and sodium fluoride (1.72 mmol, 238 mg) were added to deoxygenated dioxane (3 mL). The reaction was heated for 4 hours at 100° C. The crude reaction was chromatographed on an HPLC (C18 column). ¹H-NMR (CDCl₃, 500 MHz) δ 8.96 (s, 2H), 8.15 (d, 1H), 7.49 (s, 1H), 7.3-7.4 (m, 3H), 2.78 (s, 3H), 2.62 (s, 3H). MS (ESI) 292.02 (M+H⁺).

The following compounds were prepared using a similar method as described in Example 13 for 2-(2-methylphenyl)-5-[(2-methyl-1,3-thiazol-4-yl)ethynyl]pyrimidine:

Example 14

5-[(2-methyl-1,3-thiazol-4-yl)ethynyl]-2-[2-(methylthio)phenyl]pyrimidine

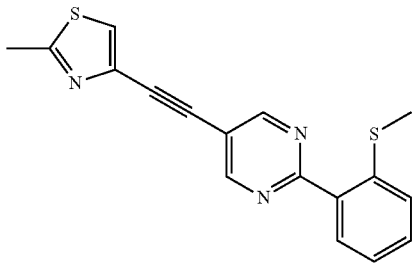

¹H-NMR (CDCl₃, 500 MHz) δ 9.0 (s, 2H), 7.89 (d, 1H), 7.49 (s, 1H), 7.1-7.3 (m, 3H), 2.78 (s, 3H), 2.49 (s, 3H). MS (ESI) 323.90 (M+H⁺).

Example 15

2-(2-chlorophenyl)-5-[(2-methyl-1,3-thiazol-4-yl)ethynyl]pyrimidine

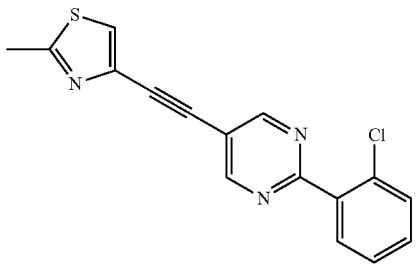 [SMILES: Cc1nc(C#Cc2cnc(-c3ccccc3Cl)nc2)cs1]

¹H-NMR (CDCl₃, 500 MHz) δ 9.0 (s, 2H), 7.81 (d, 1H), 7.3-7.5 (m, 4H), 2.78 (s, 3H). MS (ESI) 311.88 (M+H⁺).

Example 16

2-(2,3-dimethylphenyl)-5-[(2-methyl-1,3-thiazol-4-yl)ethynyl]pyrimidine

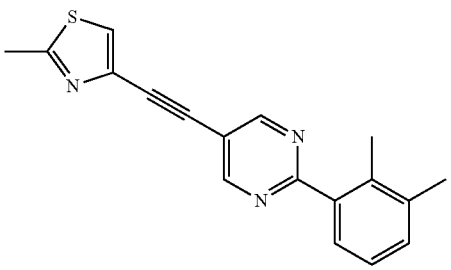

¹H-NMR (CDCl₃, 500 MHz) δ 9.0 (s, 2H), 7.81 (d, 1H), 7.1-7.5 (m, 4H), 2.78 (s, 3H), 2.4 (s, 6H). MS (ESI) 305.95 (M+H⁺).

Example 17

1-{5-[(2-methyl-1,3-thiazol-4-yl)ethynyl]pyridin-2-yl}-1H-pyrrolo[2,3-b]pyridine

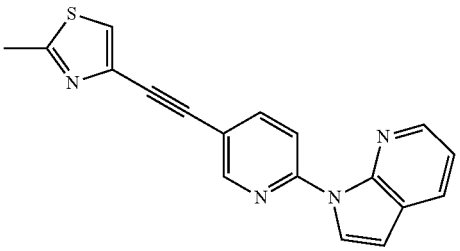 [SMILES: Cc1nc(C#Cc2ccc(-n3ccc4cccnc43)nc2)cs1]

To a stirred solution of 1H-pyrrolo[2,3-b]pyridine (2.0 mmol, 236 mg) in DMF (20 mL) at 60° C. was added sodium hydride (2.5 mmol, 100 mg of 60% wt dispersion in mineral oil). After 30 min, 2-chloro-5-[(2-methyl-1,3-thiazol-4-yl)ethynyl]pyridine (0.5 mmol, 117 mg) was added and the reaction was warmed to 75° C. and stirred overnight under nitrogen. The reaction was then partitioned with EtOAc:hexanes (1:1, 100 mL) and water (50 mL). The organic layer was washed with 5% NaCl (4×50 mL), then dried over MgSO₄, filtered, and concentrated in vacuo. The crude residue was chromatographed on SiO₂, eluting with 3% MeOH in DCM, to afford the title compound as a white solid that was dissolved in ether and precipitated as the hydrochloride salt with 1N HCl in ether. ¹H-NMR (CD₃OD, 500 MHz) δ 8.88 (m, 2H), 8.65 (d, 1H), 8.54 (d, 1H), 8.30 (dd, 1H), 8.05 (d, 1H), 7.94 (s, 1H), 7.83 (dd, 1H), 7.24 (d, 1H), 2.82 (s, 3H). MS (ESI) 317.4 (M+H⁺).

Example 18

1-{5-[(2-methyl-1,3-thiazol-4-yl)ethynyl]pyridin-2-yl}-1H-pyrrolo[2,3-c]pyridine

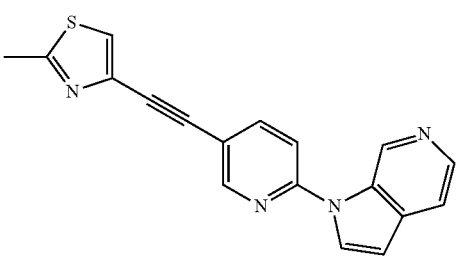 [SMILES: Cc1nc(C#Cc2ccc(-n3ccc4ccncc43)nc2)cs1]

6-azaindole hydrobromide (198 mg, 1.0 mmol), 2-chloro-5-[(2-methyl-1,3-thiazol-4-yl)ethynyl]pyridine (1.0 mmol, 234 mg), and cesium carbonate (3.2 mmol, 1.04 g) were combined in DMF (15 mL) and heated at 120° C. for 18 hrs. The reaction was cooled to room temperature and partitioned in a separatory funnel with 1:1 hexanes:EtOAc (100 mL) and water (50 mL). The organic layer was washed with 5% NaCl (4×25 mL), then dried over MgSO$_4$, filtered, and concentrated in vacuo. The crude residue was purified on SiO$_2$, elution with a 0% to 6% iPrOH gradient in DCM to afford the title compound as a white solid which was dissolved in ether and precipitated as the hydrochloride salt with 1M HCl in ether. $^1$H-NMR (CD$_3$OD, 500 MHz) δ 10.1 (s, 1H), 8.83 (m, 2H), 8.43 (d, 1H), 8.27 (d, 1H), 8.22 (d, 1H), 7.99 (d, 1H), 7.92 (s, 1H), 7.26 (d, 1H), 2.79 (s, 3H). MS (ESI) 317.2 (M+H)$^+$.

Example 19

5-[(2-methyl-1,3-thiazol-4-yl)ethynyl]-2-piperidin-1-ylpyridine

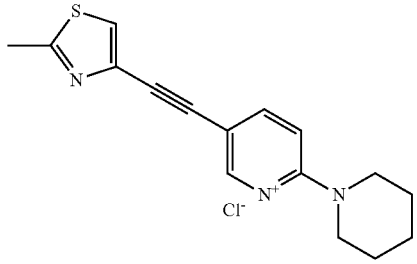 [SMILES: Cc1nc(C#Cc2ccc(N3CCCCC3)[nH+]c2)cs1 ; [Cl-]]

200 mg (0.85 mmol, 1 eq) 2-chloro-5-[(2-methyl-1,3-thiazol-4-yl)ethynyl]pyridine, 0.25 mL (2.5 mmol, 3 eq) piperidine and 2 mL DMF were combined. The reaction mixture was heated at 90° C. for 16 h, quenched with pH 10 PBS, extracted with DCM. Silica gel chromatography (gradient 10% to 50% EtOAc/Hexanes) gave 5-[(2-methyl-1,3-thiazol-4-yl)ethynyl]-2-piperidin-1-ylpyridine (L-001106455). The mono HCl salt was made by dissolving the free base into diethyl ether, adding 1 eq of HCl, and isolated by filtration. LC-MS calculated for C$_{16}$H$_{17}$N$_3$S 283, observed m/e 284.3 (M+H)$^+$. $^1$H-NMR (500 MHz, DMSO-d6) δ 8.20 (s, 1H), 7.92-7.93 (m, 2H), 7.30 (d, 1H), 3.73 (m, 4H), 2.68 (s, 3H), 1.61-1.66 (m, 6H).

Example 20

2-(2-methylpyrrolidin-1-yl)-5-[(2-methyl-1,3-thiazol-4-yl)ethynyl]pyridine

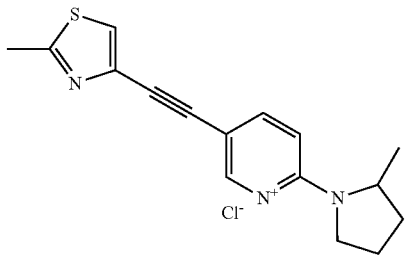 [SMILES: Cc1nc(C#Cc2ccc(N3CCCC3C)[nH+]c2)cs1 ; [Cl-]]

200 mg (0.85 mmol, 1 eq) 2-chloro-5-[(2-methyl-1,3-thiazol-4-yl)ethynyl]pyridine, 0.30 mL (2.5 mmol, 3 eq) 2-methylpyrrolidine and 2 mL NMP were combined. The reaction mixture was heated in the microwave at 180° C. for 30 min, quenched with pH 10 PBS, extracted with DCM. Silica gel chromatography (gradient 10% to 50% EtOAc/Hexanes) gave 2-(2-methylpyrrolidin-1-yl)-5-[(2-methyl-1,3-thiazol-4-yl)ethynyl]pyridine (L-001120970). The mono HCl salt was made by dissolving the free base into diethyl ether, adding 1 eq of HCl, and isolated by filtration. LC-MS calculated for C$_{16}$H$_{17}$N$_3$S 283, observed m/e 284.0 (M+H)$^+$.

Example 21

2-(2-methylpyrrolidin-1-yl)-5-[(2-methyl-1,3-thiazol-4-yl)ethynyl]pyrimidine

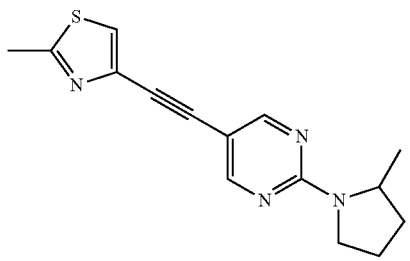 [SMILES: Cc1nc(C#Cc2cnc(N3CCCC3C)nc2)cs1]

117 mg (0.50 mmol, 1 eq) 2-chloro-5-[(2-methyl-1,3-thiazol-4-yl)ethynyl]pyrimidine, 0.50 mL (5 mmol, 10 eq) 2-methylpyrrolidine and 1 mL NMP were combined. The reaction mixture was heated at 200° C. for 15 min, quenched with pH 10 PBS, extracted with DCM. Silica gel chromatography (gradient 10% to 40% EtOAc/Hexanes) gave 2-(2-methylpyrrolidin-1-yl)-5-[(2-methyl-1,3-thiazol-4-yl)ethynyl]pyrimidine (L-001152863). LC-MS calculated for C$_{15}$H$_{16}$N$_4$S 284, observed m/e 285.3 (M+H)$^+$.

Example 22

N-(tert-butyl)-5-[(2-methyl-1,3-thiazol-4-yl)ethynyl]pyrimidin-2-amine

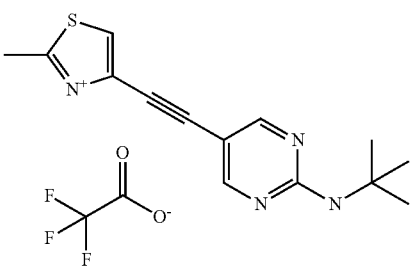 [SMILES: Cc1[nH+]c(C#Cc2cnc(NC(C)(C)C)nc2)cs1 ; O=C([O-])C(F)(F)F]

117 mg (0.50 mmol, 1 eq) 2-chloro-5-[(2-methyl-1,3-thiazol-4-yl)ethynyl]pyrimidine, 0.50 mL (5 mmol, 10 eq) t-butyl amine and 1 mL NMP were combined. The reaction mixture was heated at 180° C. for 10 min. The reaction mixture was purified without workup. Preparative reverse phase HPLC (gradient 30% to 100% MeCN/water) gave N-(tert-butyl)-5-[(2-methyl-1,3-thiazol-4-yl)ethynyl]pyrimidin-2-amine as the TFA salt. LC-MS calculated for C$_{14}$H$_{16}$N$_4$S 272, observed m/e 273.2 (M+H)$^+$.

The following compounds were prepared using a similar method as described in Example 22 for N-(tert-butyl)-5-[(2-methyl-1,3-thiazol-4-yl)ethynyl]pyrimidin-2-amine.

Example 23

2-(3-methylpiperidin-1-yl)-5-[(2-methyl-1,3-thiazol-4-yl)ethynyl]pyrimidine

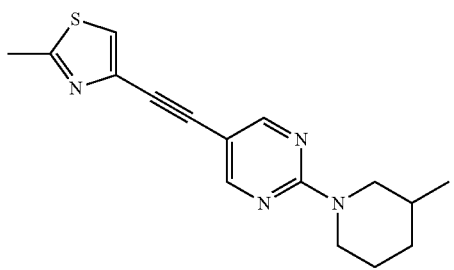

$^1$H-NMR (CDCl$_3$, 300 MHz) δ 8.46 (s, 2H), 7.35 (s, 1H), 4.63 (m, 2H), 2.94 (t, 1H), 2.75 (s, 3H), 2.60 (m, 1H), 1.88 (bs), 1.78 (m, 1H), 1.65 (m, 1H), 1.55 (m, 1H), 1.22 (m, 1H), 0.98 (d, 3H). MS (ESI) 299.16 (M+H$^+$).

Example 24

5-[(2-methyl-1,3-thiazol-4-yl)ethynyl]-2-piperidin-1-ylpyrimidine

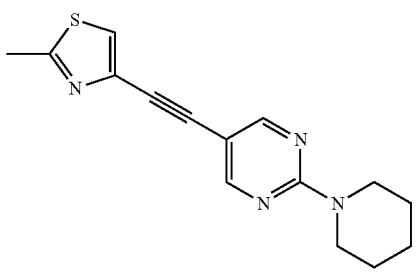 [SMILES: Cc1nc(C#Cc2cnc(N3CCCCC3)nc2)cs1]

$^1$H-NMR (CDCl$_3$, 300 MHz) δ 8.46 (s, 2H), 7.35 (s, 1H), 3.85 (m, 4H), 2.75 (s, 3H), 2.60 (m, 1H), 1.69 (m, 2H), 1.63 (m, 4H). MS (ESI) 285.14 (M+H$^+$).

Example 25

2-isopropoxy-5-[(2-methyl-1,3-thiazol-4-yl)ethynyl]pyrimidine

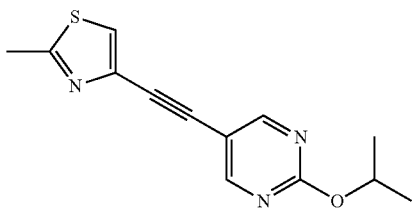 [SMILES: Cc1nc(C#Cc2cnc(OC(C)C)nc2)cs1]

50 mg 2-chloro-5-[(2-methyl-1,3-thiazol-4-yl)ethynyl]pyrimidine, 200 mg potassium carbonate and 5 mL isopropanol were combined. The reaction mixture was heated at 80° C. for 1 h. RPHPLC gave 5-[(2-methyl-1,3-thiazol-4-yl)ethynyl]-2-isopropoxy-1-ylpyrimidine. $^1$H-NMR (500 MHz, CDCl$_3$) δ 8.20 (s, 1H), 8.70 (s, 2H), 7.45 (s, 1H), 5.36 (m, 1H), 2.81 (s, 3H), 1.44 (d, 6H). MS (ESI) 259.88 (M+H)$^+$ The following compounds were prepared using a similar method as described in Example 25 for 2-isopropoxy-5-[(2-methyl-1,3-thiazol-4-yl)ethynyl]pyrimidine:

Example 26

2-isopropoxy-5-[(2-methyl-1,3-thiazol-4-yl)ethynyl]pyridinium trifluoroacetate

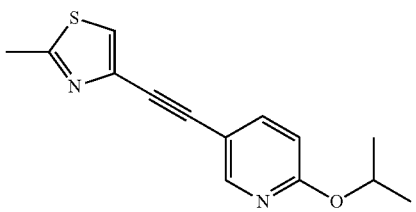 [SMILES: Cc1nc(C#Cc2ccc(OC(C)C)nc2)cs1]

MS (ESI) 259 (M+H)$^+$

Example 27

2-tert-butoxy-5-[(2-methyl-1,3-thiazol-4-yl)ethynyl]pyridine

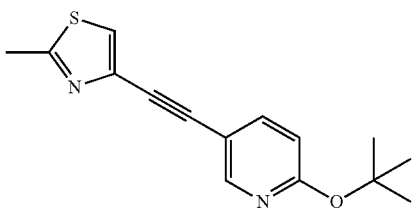 [SMILES: Cc1nc(C#Cc2ccc(OC(C)(C)C)nc2)cs1]

$^1$H NMR (CDCl$_3$ 500 MHz) δ 8.315-8.310 (d, 1H), 7.644-7.622 (dd, 1H), 7.34 (s, 1H), 6.61-6.60 (d, 1H), 2.73 (s, 1H), 1.59 (s, 9H). MS (ESI) 273.06 (M$^+$+H).

Example 28

2-(tert-butylthio)-5-[(2-methyl-1,3-thiazol-4-yl)ethynyl]pyridine

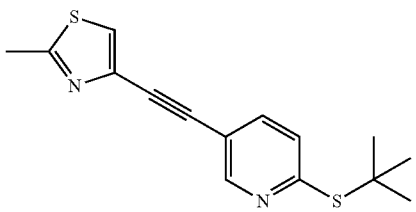 [SMILES: Cc1nc(C#Cc2ccc(SC(C)(C)C)nc2)cs1]

$^1$H NMR (CDCl$_3$ 500 MHz) δ 8.580-8.576 (d, 1H), 7.56-7.54 (dd, 1H), 7.34 (s, 1H), 7.18-7.17 (d, 1H), 2.69 (s, 3H), 1.49 (s, 9H). MS 289.14 (M$^+$+H).

Example 29

2-(tert-butylthio)-5-[(2-methyl-1,3-thiazol-4-yl)ethynyl]pyrimidine as white solid

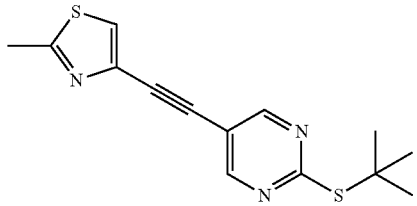 [SMILES: Cc1nc(C#Cc2cnc(SC(C)(C)C)nc2)cs1]

$^1$H NMR (MeOD$_4$ 500 MHz) 8.73 (s, 2H), 7.98 (s, 1H), 2.86 (s, 3H), 1.63 (s, 9H). MS (ESI) 290.03 (M$^+$+H).

Example 30

2-cyclohexyl-5-[(2-methyl-1,3-thiazol-4-yl)ethynyl]pyridine

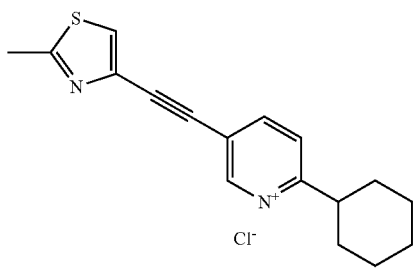 [SMILES: Cc1nc(C#Cc2ccc(C3CCCCC3)[nH+]c2)cs1 ; [Cl-]]

200 mg (0.85 mmol, 1 eq) 2-chloro-5-[(2-methyl-1,3-thiazol-4-yl)ethynyl]pyridine, 50 mg (0.043 mmol, 0.05 eq) tetrakis(triphenylphosphine)palladium(0), and 2 mL of 0.5 M cyclohexylzinc bromide in THF (1 mmol, 1.1 eq) were combined. The reaction mixture was heated at 150° C. in the microwave for 5 min, quenched with pH 7 PBS, extracted with DCM. Silica gel chromatography (gradient 0% to 40% EtOAc/Hexanes) gave 2-cyclohexyl-5-[(2-methyl-1,3-thiazol-4-yl)ethynyl]pyridine (L-001106449). The mono HCl salt was made by dissolving the free base into diethyl ether, adding 1 eq of HCl, and isolated by filtration. LC-MS calculated for C$_{17}$H$_{18}$N$_2$S 282, observed m/e 283.3 (M+H)$^+$. $^1$H-NMR (500 MHz, DMSO-d6) δ 8.87 (s, 1H), 8.30 (d, 1H), 8.03 (s, 1H), 7.71 (d, 1H), 2.94 (m, 1H), 2.69 (s, 3H), 1.35-1.91 (m, 10H).

Example 31

2-tert-butyl-5-[(2-methyl-1,3-thiazol-4-yl)ethynyl]pyridine

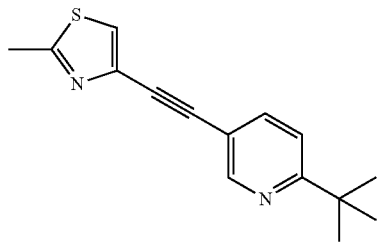 [SMILES: Cc1nc(C#Cc2ccc(C(C)(C)C)nc2)cs1]

200 mg (0.85 mmol, 1 eq) 2-chloro-5-[(2-methyl-1,3-thiazol-4-yl)ethynyl]pyridine, 50 mg (0.043 mmol, 0.05 eq) tetrakis(triphenylphosphine)palladium(0), and 2 mL of 0.5 M t-butylzinc bromide in THF (1 mmol, 1.1 eq) were combined. The reaction mixture was heated at 150° C. in the microwave for 5 min, quenched with pH 10 PBS, extracted with DCM. Silica gel chromatography (gradient 5% to 50% EtOAc/Hexanes) gave 2-tert-butyl-5-[(2-methyl-1,3-thiazol-4-yl)ethynyl]pyridine (L-001109555). LC-MS calculated for C$_{15}$H$_{16}$N$_2$S 256, observed m/e 257.0 (M+H)$^+$. $^1$H-NMR (500 MHz, CDCl$_3$) δ 8.74 (s, 1H), 7.76 (d, 1H), 7.45 (s, 1H), 7.12 (d, 1H), 2.77 (s, 3H), 2.12 (m, 1H), 0.97 (d, 9H).

Example 32

2-cyclohexyl-5-[(2-methyl-1,3-thiazol-4-yl)ethynyl]pyrimidine

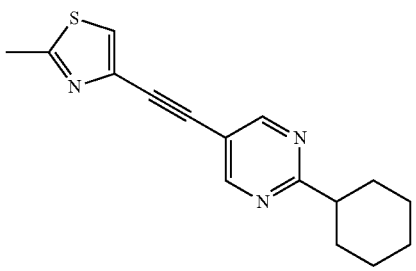 [SMILES: Cc1nc(C#Cc2cnc(C3CCCCC3)nc2)cs1]

200 mg (0.85 mmol, 1 eq) 2-chloro-5-[(2-methyl-1,3-thiazol-4-yl)ethynyl]pyrimidine, 50 mg (0.043 mmol, 0.05 eq) tetrakis(triphenylphosphine)palladium(0), and 2 mL of 0.5 M cyclohexylzinc bromide in THF (1 mmol, 1.1 eq) were combined. The reaction mixture was heated at 150° C. in the microwave for 5 min, quenched with pH 10 PBS, extracted with DCM. Silica gel chromatography (gradient 10% to 40% EtOAc/Hexanes) gave 2-cyclohexyl-5-[(2-methyl-1,3-thiazol-4-yl)ethynyl]pyrimidine (L-001152744). LC-MS calculated for C$_{16}$H$_{17}$N$_3$S 283, observed m/e 284.1 (M+H)$^+$.

Examples 33-107

Using synthetic techniques similar to those described above and well known to those skilled in the art, the following compounds were prepared:

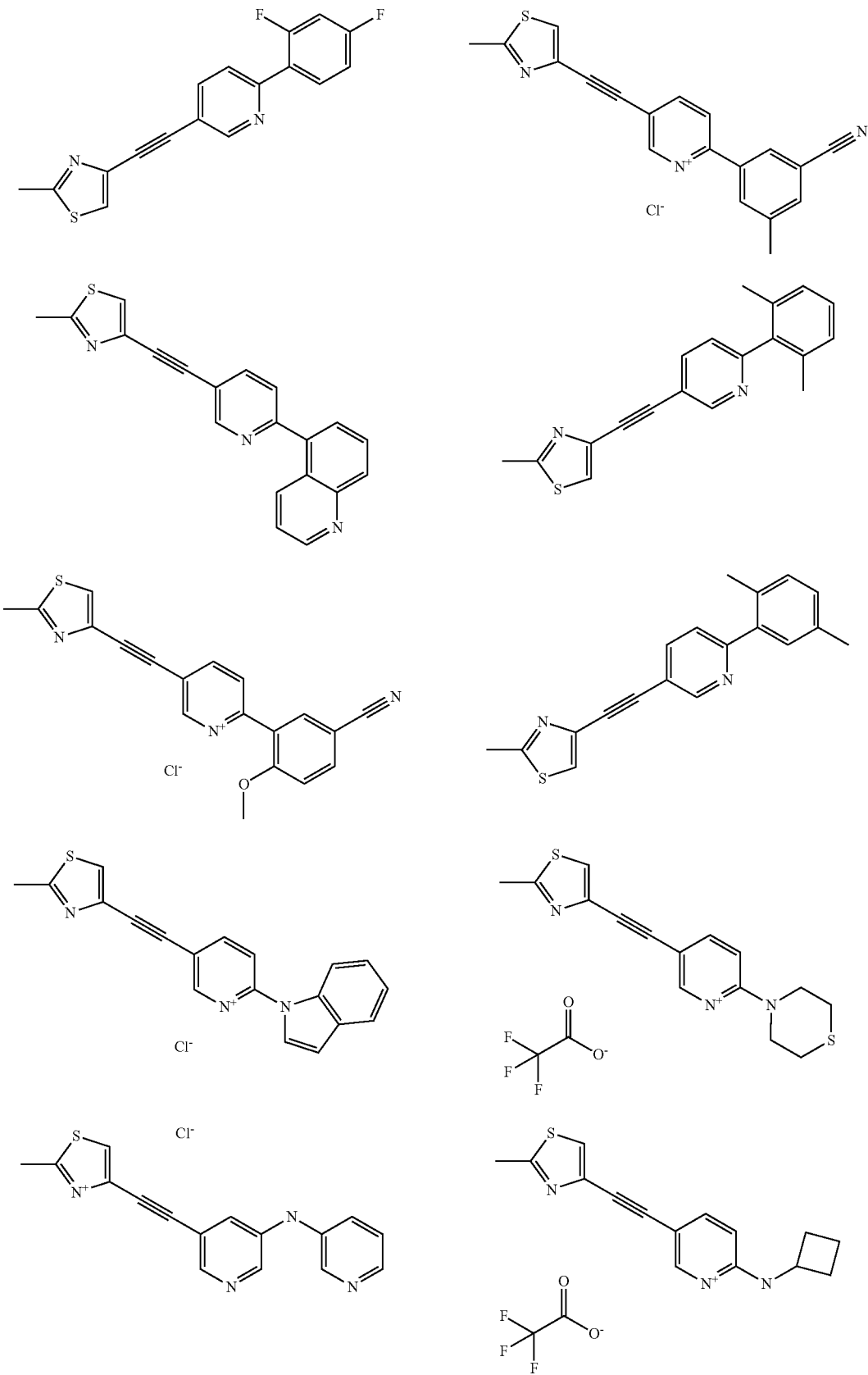

-continued
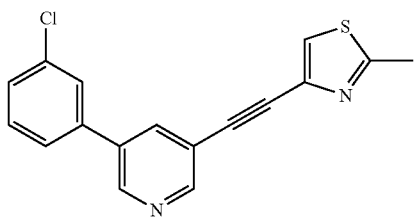 [SMILES: Cc1nc(C#Cc2cncc(-c3cccc(Cl)c3)c2)cs1]
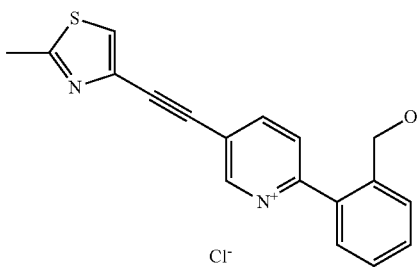 [SMILES: Cc1nc(C#Cc2ccc(-c3ccccc3CO)[nH+]c2)cs1 ; [Cl-]]
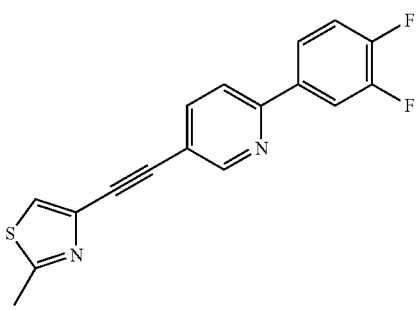 [SMILES: Cc1nc(C#Cc2ccc(-c3ccc(F)c(F)c3)nc2)cs1]
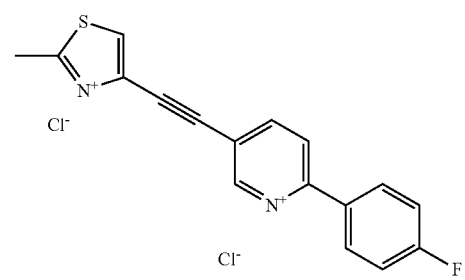 [SMILES: Cc1[nH+]c(C#Cc2ccc(-c3ccc(F)cc3)[nH+]c2)cs1 ; [Cl-] ; [Cl-]]
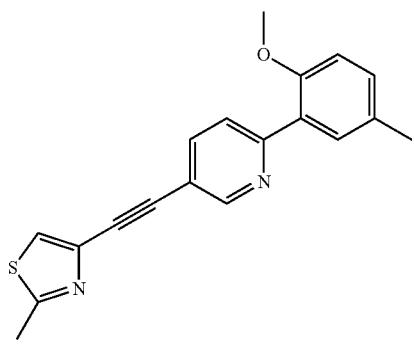 [SMILES: COc1ccc(C)cc1-c1ccc(C#Cc2csc(C)n2)cn1]
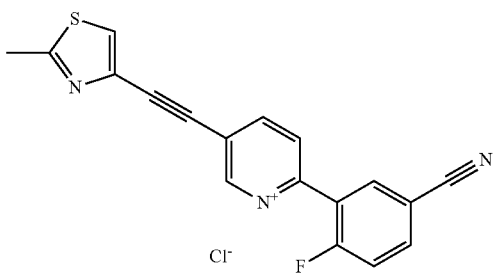 [SMILES: Cc1nc(C#Cc2ccc(-c3cc(C#N)ccc3F)[nH+]c2)cs1 ; [Cl-]]
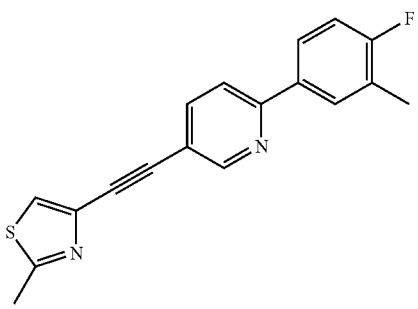 [SMILES: Cc1nc(C#Cc2ccc(-c3ccc(F)c(C)c3)nc2)cs1]
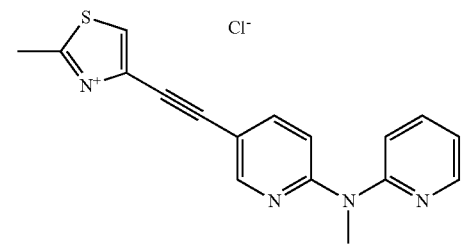 [SMILES: Cc1[nH+]c(C#Cc2ccc(N(C)c3ccccn3)nc2)cs1 ; [Cl-]]
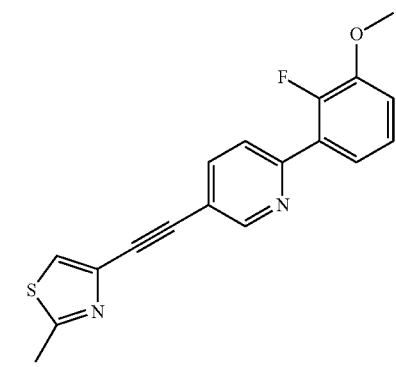 [SMILES: COc1cccc(-c2ccc(C#Cc3csc(C)n3)cn2)c1F]
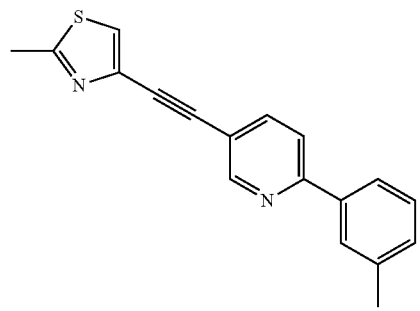 [SMILES: Cc1cccc(-c2ccc(C#Cc3csc(C)n3)cn2)c1]

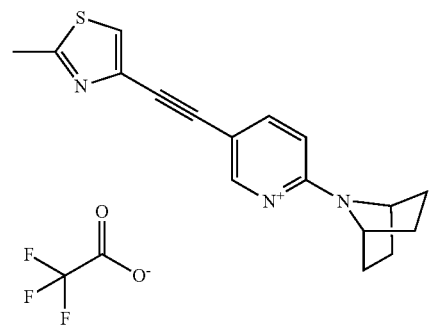 [SMILES: Cc1nc(C#Cc2ccc(N3C4CCC3CC4)[nH+]c2)cs1 ; O=C([O-])C(F)(F)F]
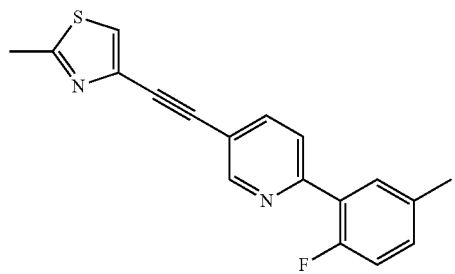
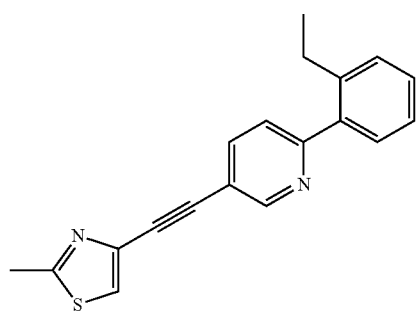 [SMILES: CCc1ccccc1-c1ccc(C#Cc2csc(C)n2)cn1]
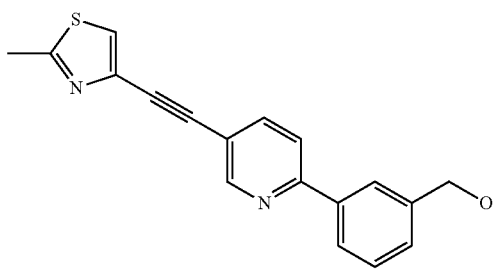 [SMILES: Cc1nc(C#Cc2ccc(-c3cccc(CO)c3)nc2)cs1]
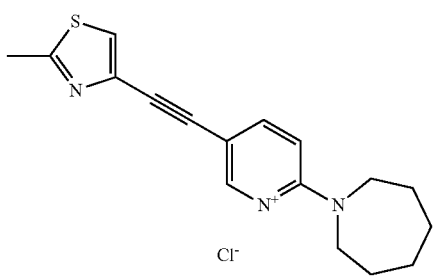 [SMILES: Cc1nc(C#Cc2ccc(N3CCCCCC3)[nH+]c2)cs1 ; [Cl-]]
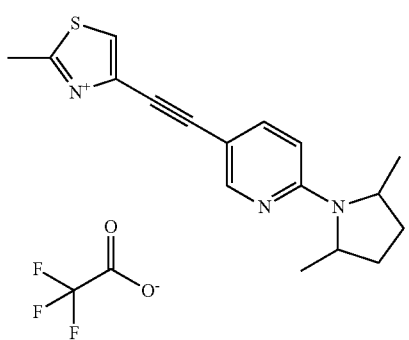 [SMILES: Cc1[nH+]c(C#Cc2ccc(N3C(C)CCC3C)nc2)cs1 ; O=C([O-])C(F)(F)F]
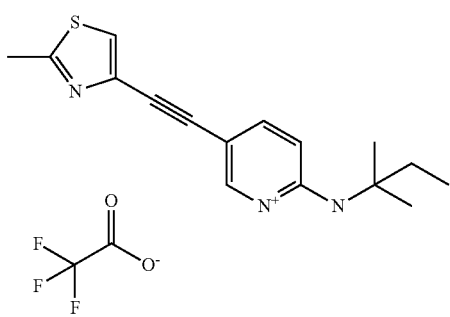 [SMILES: CCC(C)(C)Nc1ccc(C#Cc2csc(C)n2)c[nH+]1 ; O=C([O-])C(F)(F)F]
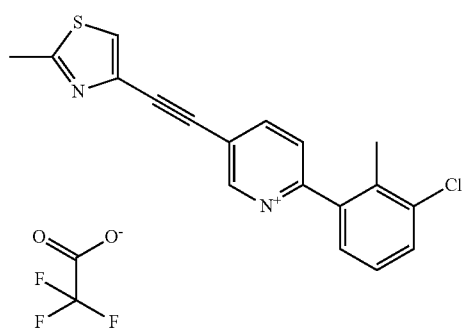 [SMILES: Cc1nc(C#Cc2ccc(-c3cccc(Cl)c3C)[nH+]c2)cs1 ; O=C([O-])C(F)(F)F]
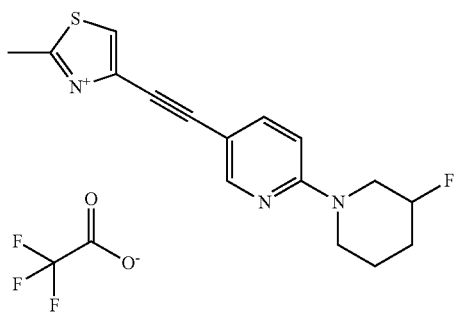 [SMILES: Cc1[nH+]c(C#Cc2ccc(N3CCCC(F)C3)nc2)cs1 ; O=C([O-])C(F)(F)F]
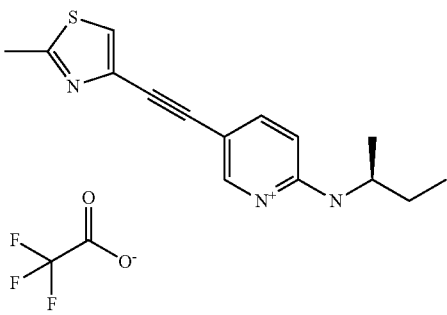 [SMILES: CC[C@H](C)Nc1ccc(C#Cc2csc(C)n2)c[nH+]1 ; O=C([O-])C(F)(F)F]

-continued
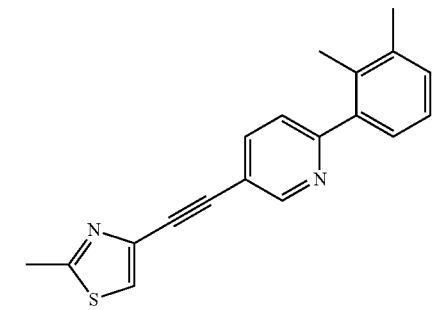 [SMILES: Cc1nc(C#Cc2ccc(-c3cccc(C)c3C)nc2)cs1]
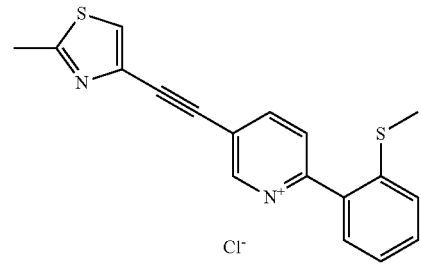
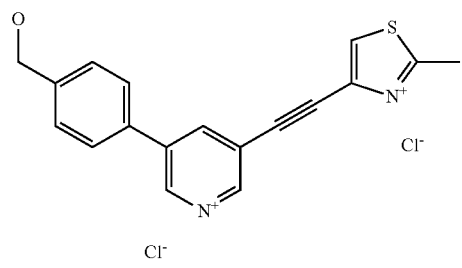 [SMILES: Cc1[nH+]c(C#Cc2c[nH+]cc(-c3ccc(CO)cc3)c2)cs1 ; [Cl-] ; [Cl-]]
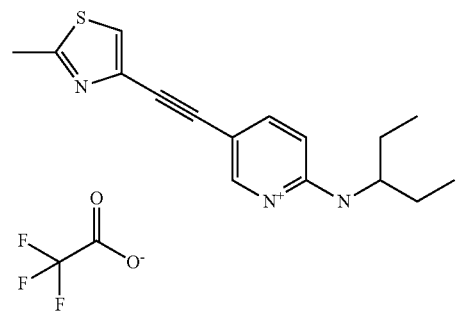 [SMILES: CCC(CC)Nc1ccc(C#Cc2csc(C)n2)c[nH+]1 ; O=C([O-])C(F)(F)F]
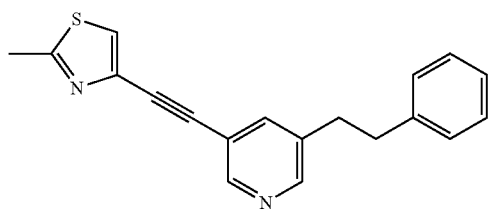 [SMILES: Cc1nc(C#Cc2cncc(CCc3ccccc3)c2)cs1]
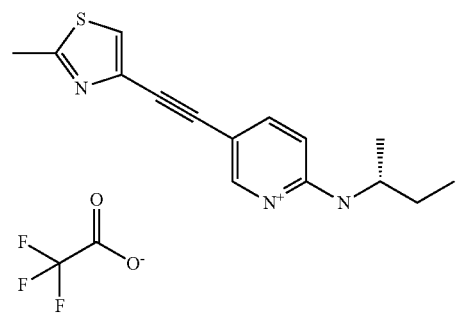 [SMILES: CC[C@@H](C)Nc1ccc(C#Cc2csc(C)n2)c[nH+]1 ; O=C([O-])C(F)(F)F]
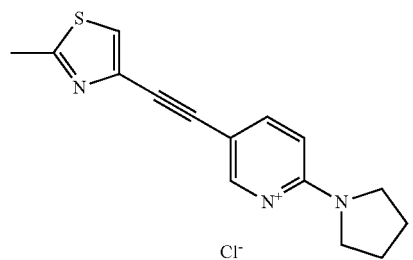 [SMILES: Cc1nc(C#Cc2ccc(N3CCCC3)[nH+]c2)cs1 ; [Cl-]]
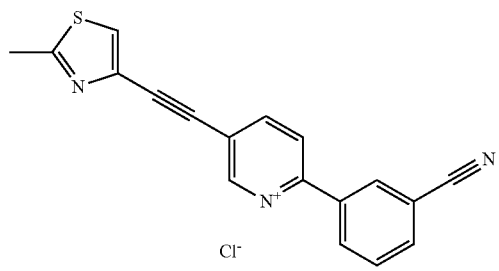 [SMILES: Cc1nc(C#Cc2ccc(-c3cccc(C#N)c3)[nH+]c2)cs1 ; [Cl-]]
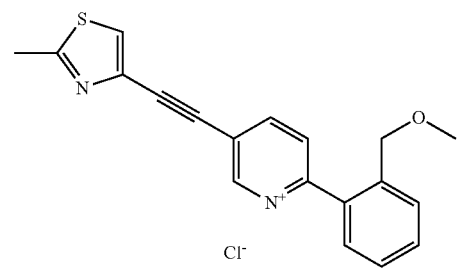
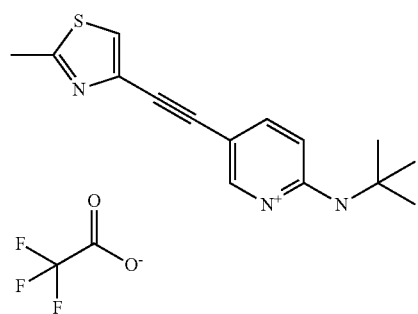 [SMILES: Cc1nc(C#Cc2ccc(NC(C)(C)C)[nH+]c2)cs1 ; O=C([O-])C(F)(F)F]

-continued
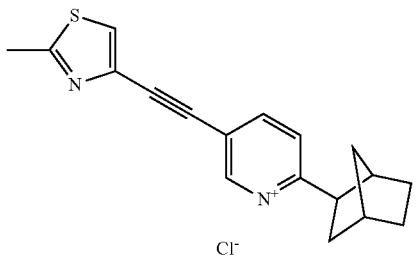 [SMILES: Cc1nc(C#Cc2ccc(C3CC4CCC3C4)[nH+]c2)cs1 ; [Cl-]]
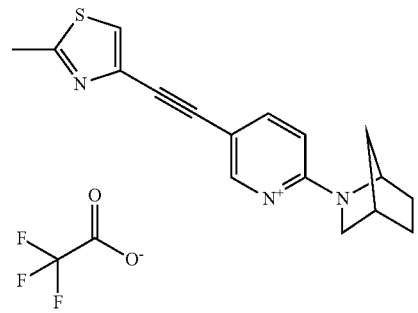 [SMILES: Cc1nc(C#Cc2ccc(N3CC4CCC3C4)[nH+]c2)cs1 ; O=C([O-])C(F)(F)F]
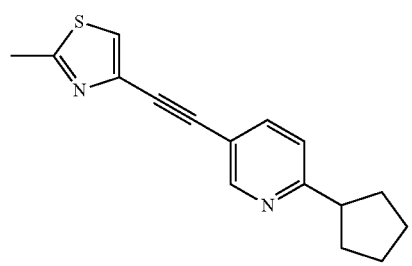 [SMILES: Cc1nc(C#Cc2ccc(C3CCCC3)nc2)cs1]
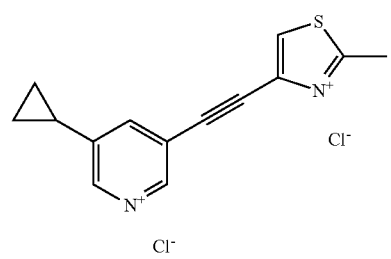 [SMILES: Cc1[nH+]c(C#Cc2c[nH+]cc(C3CC3)c2)cs1 ; [Cl-] ; [Cl-]]
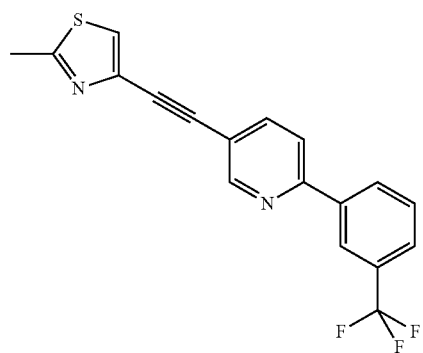 [SMILES: Cc1nc(C#Cc2ccc(-c3cccc(C(F)(F)F)c3)nc2)cs1]
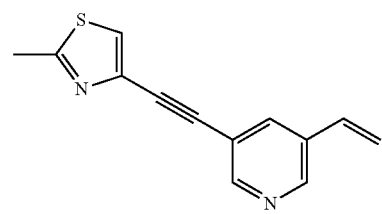 [SMILES: C=Cc1cncc(C#Cc2csc(C)n2)c1]
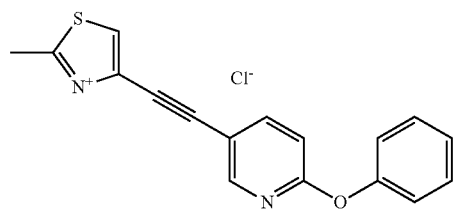 [SMILES: Cc1[nH+]c(C#Cc2ccc(Oc3ccccc3)nc2)cs1 ; [Cl-]]
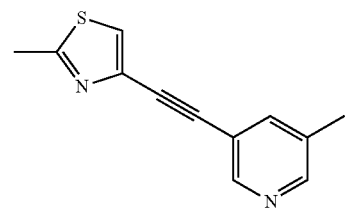
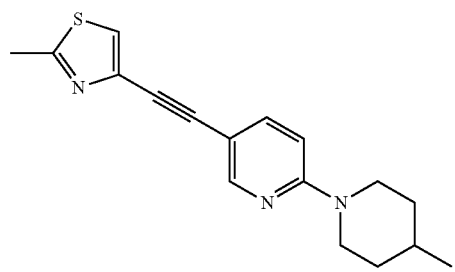
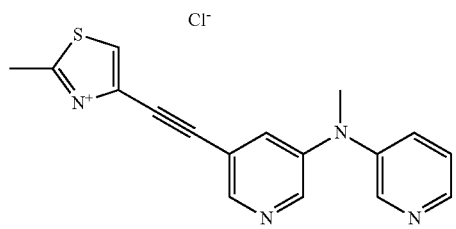 [SMILES: [Cl-] ; Cc1[nH+]c(C#Cc2cncc(N(C)c3cccnc3)c2)cs1]

-continued
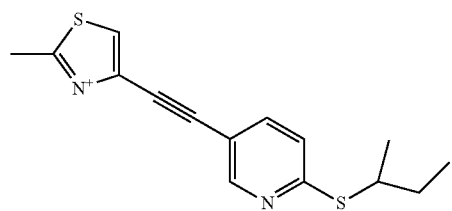 [SMILES: CCC(C)Sc1ccc(C#Cc2csc(C)[nH+]2)cn1] 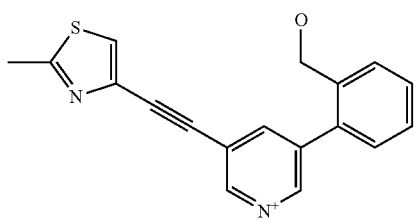
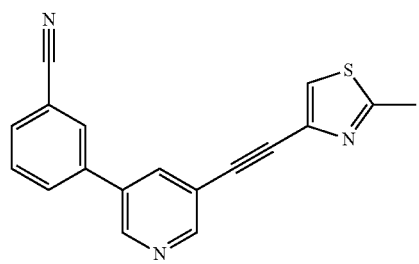 [SMILES: Cc1nc(C#Cc2cncc(-c3cccc(C#N)c3)c2)cs1] 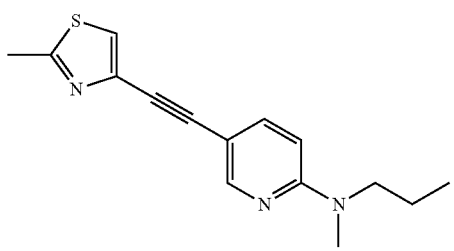 [SMILES: CCCN(C)c1ccc(C#Cc2csc(C)n2)cn1]
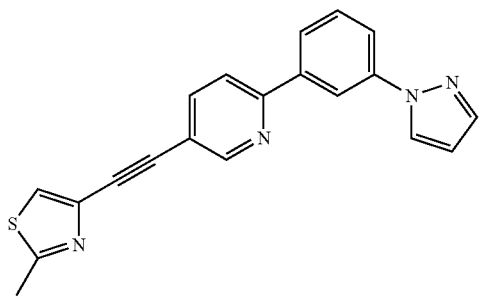 [SMILES: Cc1nc(C#Cc2ccc(-c3cccc(-n4cccn4)c3)nc2)cs1] 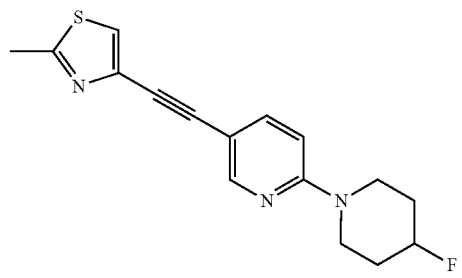 [SMILES: Cc1nc(C#Cc2ccc(N3CCC(F)CC3)nc2)cs1]
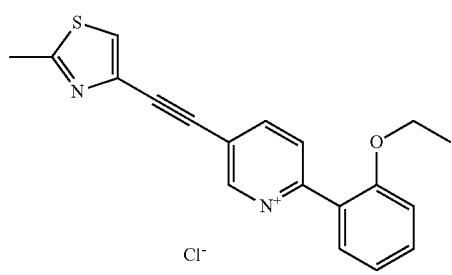 [SMILES: CCOc1ccccc1-c1ccc(C#Cc2csc(C)n2)c[nH+]1 ; [Cl-]] 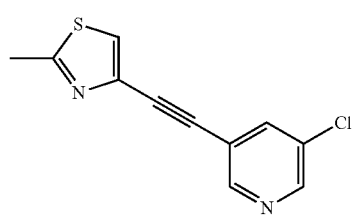
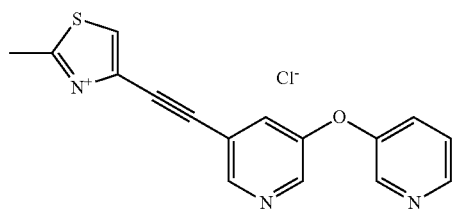 [SMILES: Cc1[nH+]c(C#Cc2cncc(Oc3cccnc3)c2)cs1 ; [Cl-]] 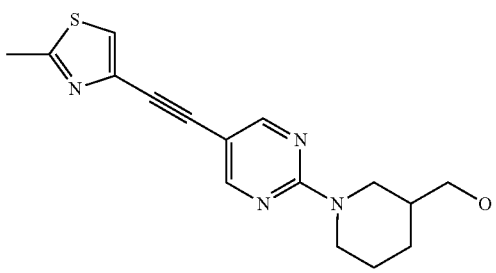 [SMILES: Cc1nc(C#Cc2cnc(N3CCCC(CO)C3)nc2)cs1]

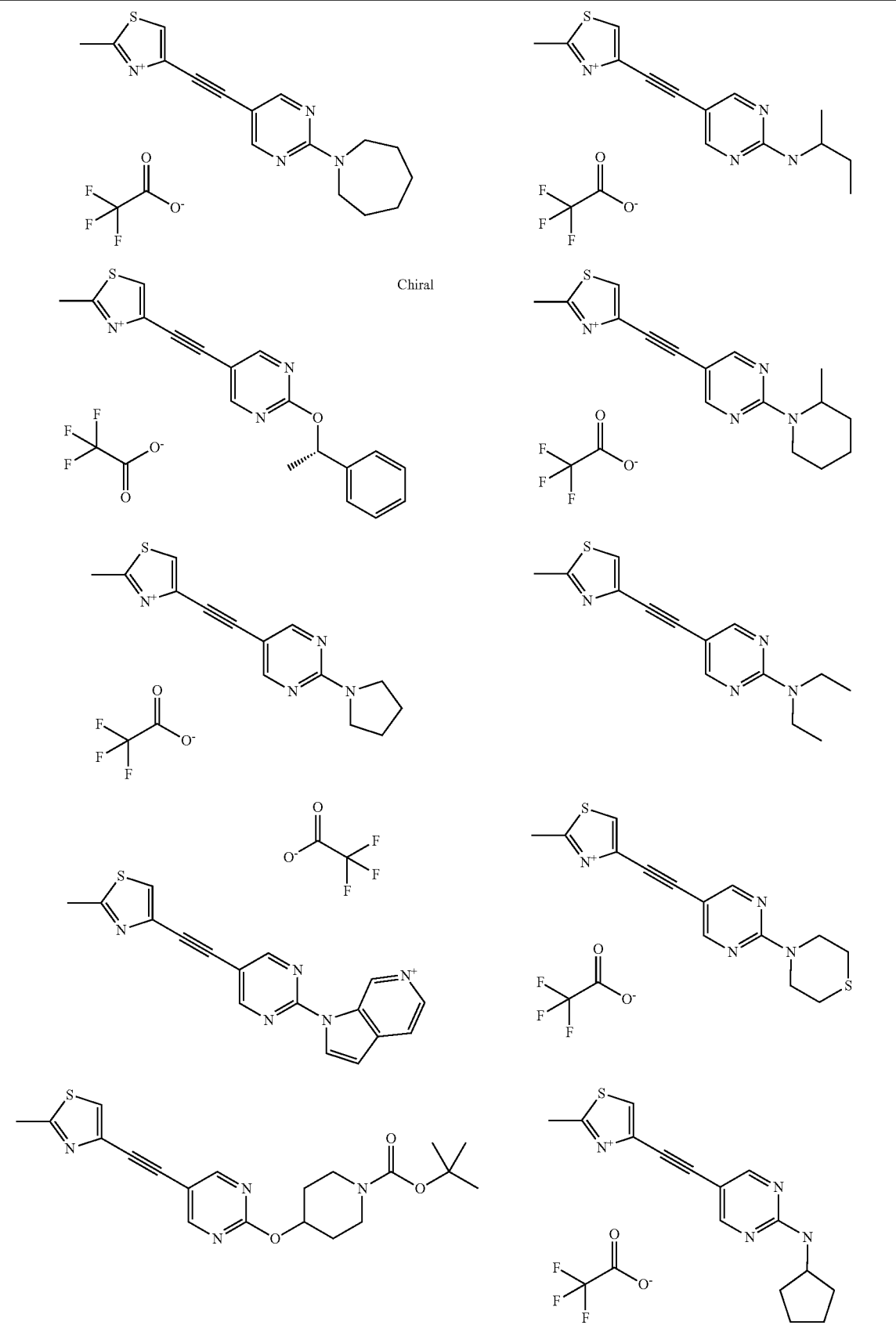

-continued

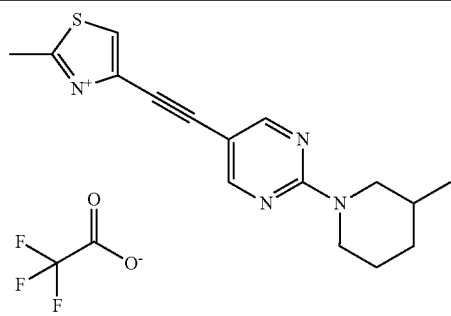
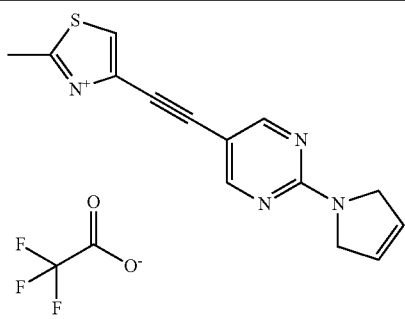
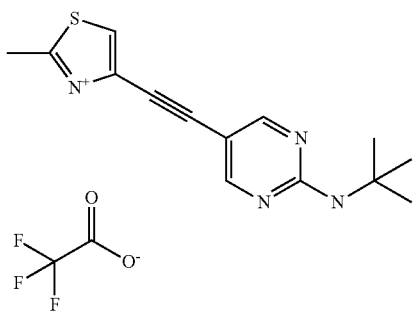 [SMILES: Cc1[nH+]c(C#Cc2cnc(NC(C)(C)C)nc2)cs1 ; O=C([O-])C(F)(F)F]
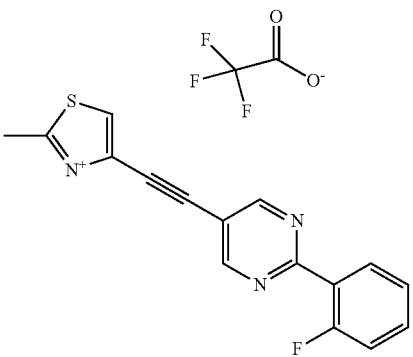 [SMILES: Cc1[nH+]c(C#Cc2cnc(-c3ccccc3F)nc2)cs1 ; O=C([O-])C(F)(F)F]
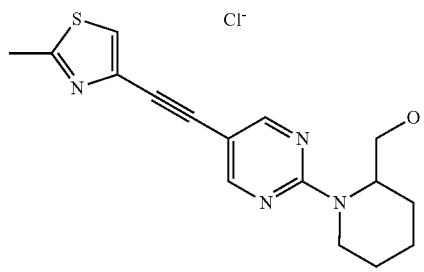 [SMILES: Cc1nc(C#Cc2cnc(N3CCCCC3CO)nc2)cs1 ; [Cl-]]

(Examples are to be read left to right across the rows of the table.)

Example 108

Calcium Flux Assay

The activity of compounds was examined against the hmGluR5a receptor stably expressed in mouse fibroblast Ltk– cells (the hmGluR5a/L38-20 cell line). See generally Daggett et al., Neuropharmacology 34:871-886 (1995). Receptor activity was detected by changes in intracellular calcium ($[Ca^{2+}]_i$) measured using the fluorescent calcium-sensitive dye, fura-2. hmGluR5a/L38-20 cells were plated onto 96-well plates, and loaded with 3 M fura-2 for 1 h. Unincorporated dye was washed from the cells, and the cell plate was transferred to a custom-built 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every 1 s, and ratio images were generated after background subtraction. After a basal reading of 20 s, an $EC_{80}$ concentration of glutamate (10 M) was added to the well, and the response evaluated for another 60 s. The glutamate-evoked increase in $[Ca^{2+}]_i$ in the presence of the screening compound was compared to the response of glutamate alone (the positive control).

Example 109

[$^3$H]-mGluR5 Antagonist Binding to Rodent Brain Membranes

In accordance with Anderson J J, Rao S P, Rowe B, Giracello D R, Holtz G, Chapman D F, Tehrani L, Bradbury M J, Cosford N D, Varney M A, [$^3$H]Methoxymethyl-3-[(2-methyl-1,3-thiazol-4-yl)ethynyl]pyridine binding to metabotropic glutamate receptor subtype 5 in rodent brain: in vitro and in vivo characterization. *J Pharmacol Exp Ther.* 2002 December; 303 (3):1044-51, membranes were prepared (as described in Ransom R W and Stec N L (1988) Cooperative modulation of [$^3$H]MK-801 binding to the N-methyl-D-aspartate receptor-ion channel complex by L-glutamate, glycine, and polyamines. *J Neurochem* 51:830-836) using whole rat brain, or mGlu5$^{+/+}$ or mGlu5$^{-/-}$ whole mouse brain.

Binding assays were performed as described in Schaffhauser H, Richards J G, Cartmell J, Chaboz S, Kemp J A, Klingelschmidt A, Messer J, Stadler H, Woltering T and Mutel V (1998) In vitro binding characteristics of a new selective group II metabotropic glutamate receptor radioligand, [³H]LY354740, in rat brain. *Mol Pharmacol* 53:228-233) at room temperature with slight modifications. Briefly, membranes were thawed and washed once with assay buffer (50 mM HEPES, 2 mM MgCl$_2$, pH 7.4), followed by centrifugation at 40,000×g for 20 min. The pellet was resuspended in assay buffer and briefly homogenized with a Polytron.

For protein linearity experiments, increasing concentrations of membrane protein were added to 96-well plates in triplicate and binding was initiated by addition of 20 nM [³H]methoxymethyl-3-[(2-methyl-1,3-thiazol-4-yl)ethynyl] pyridine. The assay was incubated for 2 h and non-specific binding was determined using 10 μM MPEP. The binding was terminated by rapid filtration through glass-fiber filters (Unifilter-96 GF/B plate, Packard) using a 96-well plate Brandel cell harvester. Following addition of scintillant, the radioactivity was determined by liquid scintillation spectrometry. Protein measurements were performed by BioRad-DC Protein assay using bovine serum albumin as the standard.

Saturation binding experiments were performed in triplicate with increasing concentrations of [³H]methoxymethyl-3-[(2-methyl-1,3-thiazol-4-yl)ethynyl]pyridine (1 pM to 100 nM). The time course of association was measured by the addition of 10 nM [³H]methoxymethyl-3-[(2-methyl-1,3-thiazol-4-yl)ethynyl]pyridine to the membranes at different time points (0-240 min), followed by filtration. Dissociation was measured by the addition of 100 μM unlabeled methoxymethyl-3-[(2-methyl-1,3-thiazol-4-yl)ethynyl]pyridine at different time points to membranes previously incubated for 3 h with 10 nM [³H]methoxymethyl-3-[(2-methyl-1,3-thiazol-4-yl)ethynyl]pyridine. For competition experiments, 100 μg membrane protein and 10 nM [³H]methoxymethyl-3-[(2-methyl-1,3-thiazol-4-yl)ethynyl]pyridine was added to wells containing increasing concentration of the test compound in duplicate (methoxymethyl-3-[(2-methyl-1,3-thiazol-4-yl)ethynyl]pyridine or MPEP). [³H]-3-Methoxy-5-(pyridin-2-ylethynyl)pyridine may also be used as the radioligand in the procedure described above. (See, Cosford, N. D. P.; Roppe, J.; Tehrani, L.; Seiders, T. J.; Schweiger, E. J. et al. [3H]-Methoxymethyl-MTEP and [3H]-methoxy-PEPy): Potent and selective radioligands for the Metabotropic Glutamate Subtype 5 (mGlu5) Receptor. *Bioorg. Med. Chem. Lett.* 2003, 13, 351-354.)

Example 110

Phosphatidylinositol Hydrolysis (IP) Assay

Inositol phophate assays were performed as described by Berridge et al. (1982) (Berridge et al, (1982) Biochem. J. 206: 587-5950; and Nakajima et al., J. Biol. Chem. 267:2437-2442 (1992)) with slight modifications. Mouse fibroblast Ltk cells expressing hmGluR5 (hmGluR5/L38-20 cells) were seeded in 24-well plates at a density of 8×105 cells/well. One Ci of [³H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 ml of standard Hepes buffered saline buffer (HBS; 125 mM NaCl, 5 mM KCl, 0.62 M MgSO$_4$, 1.8 mM CaCl$_2$, 20 mM HEPES, 6 mM glucose, pH to 7.4). The cells were washed with HBS containing 10 mM LiCl, and 400 ill buffer added to each well. Cells were incubated at 37° C. for 20 min. For testing, 50 L, of 10× compounds used in the practice of the invention [made in HBS/LiCl (100 mM)] was added and incubated for 10 minutes. Cells were activated by the addition of 10 pM glutamate, and the plates left for 1 hour at 37° C.

The incubations were terminated by the addition of 1 mL ice-cold methanol to each well. In order to isolate inositol phosphates (IPs), the cells were scraped from wells, and placed in numbered glass test tubes. Chloroform (1 mL) was added to each tube, the tubes were mixed, and the phases separated by centrifugation. IPs were separated on Dowex anion exchange columns (AG 1-X8 100-200 mesh formate form). The upper aqueous layer (750 L) was added to the Dowex columns, and the PCT/US00/23923 109 columns eluted with distilled water (3 mL). The eluents were discarded, and the columns were washed with 60 mM ammonium formate/5 mM Borax (10 mL), which was also discarded as waste. Finally the columns were eluted with 800 mM ammonium formate/0.1 M formic acid (4 mL), and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with control. Using this procedure an IC$_{50}$ value of 33 nM was obtained for Example 1 and an IC$_{50}$ value of 2 nM for Example 18.

Example 111

Activity of Representative Compounds

The activity of certain of the compounds disclosed in the previous examples is presented below (N.D.=not determined):

| Example | Calcium Flux Assay (nM) | Ki (nM) |
| --- | --- | --- |
| 1 | 3 | 20 |
| 2 | 1.0 | 2.0 |
| 3 | 0.9 | 2.7 |
| 4 | 2.2 | 2.6 |
| 5 | 6.3 | 1.0 |
| 6 | 4.4 | 1.2 |
| 7 | 1.1 | 0.7 |
| 8 | 1.0 | 0.9 |
| 9 | 1.1 | N.D. |
| 10 | 0.7 | N.D. |
| 11 | 1.3 | N.D. |
| 12 | 0.6 | 1.1 |
| 13 | 0.6 | 0.6 |
| 14 | 0.8 | 7.5 |
| 15 | 1.0 | 2.6 |
| 16 | 0.4 | 8.6 |
| 17 | 0.4 | 3.8 |
| 18 | 4.9 | 19.3 |
| 19 | 1.8 | 2.8 |
| 20 | 1.0 | 1.4 |
| 21 | 1.5 | 1.5 |
| 22 | 1.2 | 0.9 |
| 23 | 1.6 | 1.6 |
| 24 | 0.3 | 2.6 |
| 25 | 1.4 | 9.0 |
| 26 | 0.1 | 2.0 |
| 27 | 1.4 | 1.0 |
| 28 | 1.7 | 0.9 |
| 29 | 0.5 | 10 |
| 30 | 2.2 | 2.3 |
| 31 | 2.9 | 12.2 |
| 32 | 1.0 | 4.8 |
| 33 | 19 | 7 |
| 34 | 18 | 15 |
| 35 | 17 | 5 |
| 36 | 14 | 3 |
| 37 | 14 | 10 |

-continued

| Example | Calcium Flux Assay (nM) | Ki (nM) |
|---|---|---|
| 38 | 13 | 8 |
| 39 | 13 | 4 |
| 40 | 12 | 9 |
| 41 | 11 | 5 |
| 42 | 11 | 17 |
| 43 | 11 | 0.65 |
| 44 | 11 | 2 |
| 45 | 11 | 7 |
| 46 | 11 | 2 |
| 47 | 11 | 19 |
| 48 | 9 | 12.5 |
| 49 | 9 | 5.5 |
| 50 | 9 | 12 |
| 51 | 8 | 9 |
| 52 | 8 | 2 |
| 53 | 8 | 8 |
| 54 | 8 | 1.5 |
| 55 | 7 | 4 |
| 56 | 7 | 13 |
| 57 | 7 | 7.5 |
| 58 | 7 | 1.5 |
| 59 | 6 | 4 |
| 60 | 6 | 1.5 |
| 61 | 6 | 12 |
| 62 | 6 | 11 |
| 63 | 6 | 4 |
| 64 | 6 | 0.8 |
| 65 | 6 | 8 |
| 66 | 5 | 9 |
| 67 | 5 | 7 |
| 68 | 5 | 7 |
| 69 | 5 | 14 |
| 70 | 5 | 5 |
| 71 | 5 | 4.5 |
| 72 | 5 | 7 |
| 73 | 4 | 2 |
| 74 | 4 | 7.5 |
| 75 | 4 | 4 |
| 76 | 3.5 | 3 |
| 77 | 3 | 13 |
| 78 | 3 | 1.4 |
| 79 | 3 | 16 |
| 80 | 3 | 3 |
| 81 | 3 | 6 |
| 82 | 3 | 2 |
| 83 | 2 | 12 |
| 84 | 2 | 7 |
| 85 | 2 | 1 |
| 86 | 2 | 7 |
| 87 | 2 | N.D. |
| 88 | 2 | 4 |
| 89 | 1.6 | 2 |
| 90 | 1.5 | 4 |
| 91 | 1 | 1 |
| 92 | 12 | 7 |
| 93 | 11 | 3 |
| 94 | 9 | 6 |
| 95 | 8 | 9 |
| 96 | 5 | 5 |
| 97 | 5 | 13 |
| 98 | 4 | 8 |
| 99 | 2.8 | 33 |
| 100 | 2.3 | 23 |
| 101 | 2 | 24 |
| 102 | 2 | 26 |
| 103 | 1.6 | 1.6 |
| 104 | 1.5 | 6 |
| 105 | 1 | 1 |
| 106 | N.D. | 6 |
| 107 | 16 | 9 |

Nd = not determined

Note that the relatively high values in the calcium flux and binding assays, for Example 18, are counterbalanced by assay results in the IP assay (as reported in Example 110).

While the invention has been described in detail with reference to certain preferred embodiments thereof, it will be understood that modifications and variations are within the spirit and scope of that which is described and claimed.

What is claimed is:

1. A compound which is selected from the group consisting of:

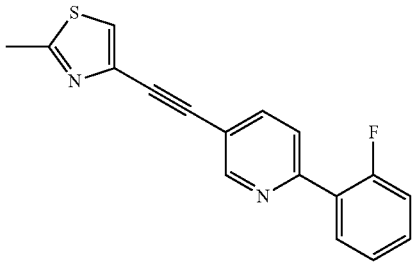

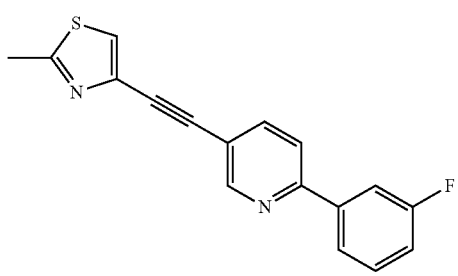

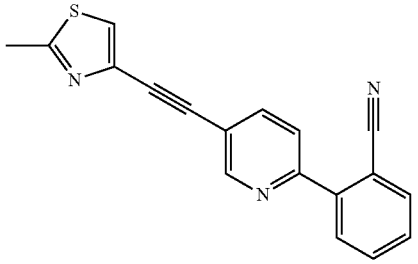

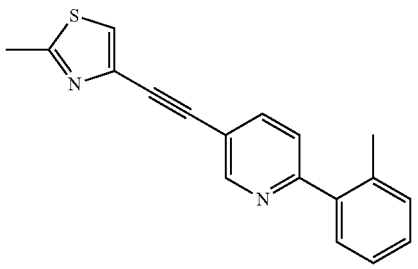

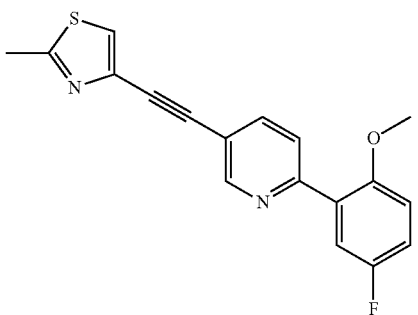

-continued
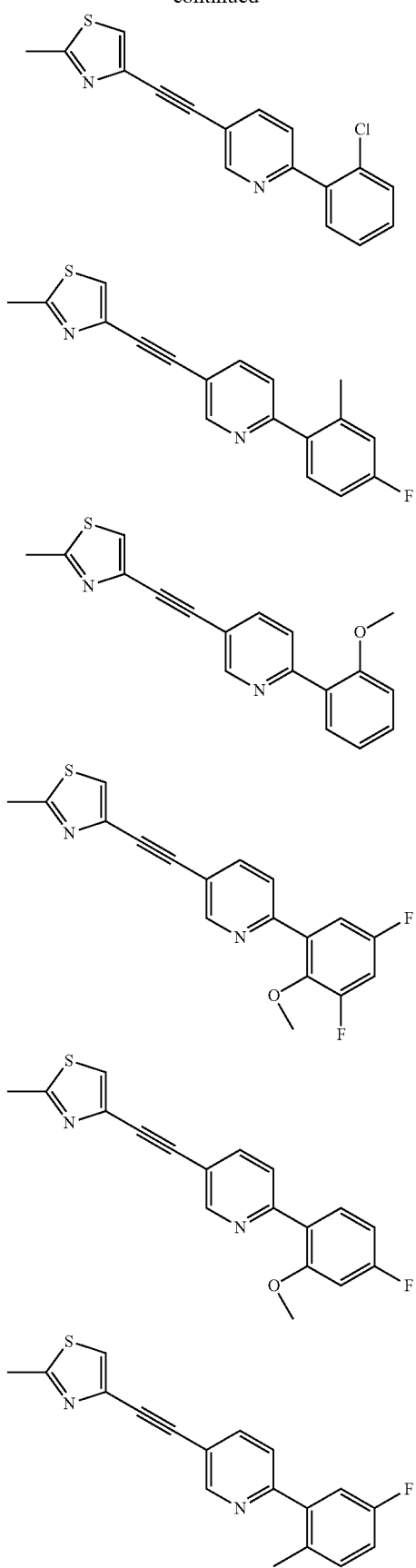
-continued
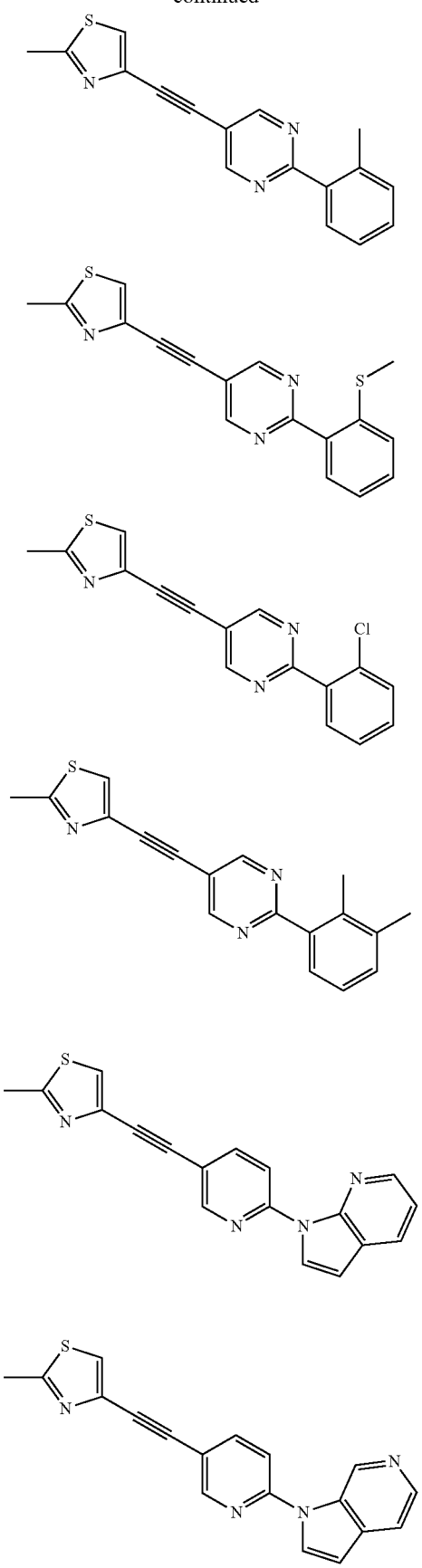

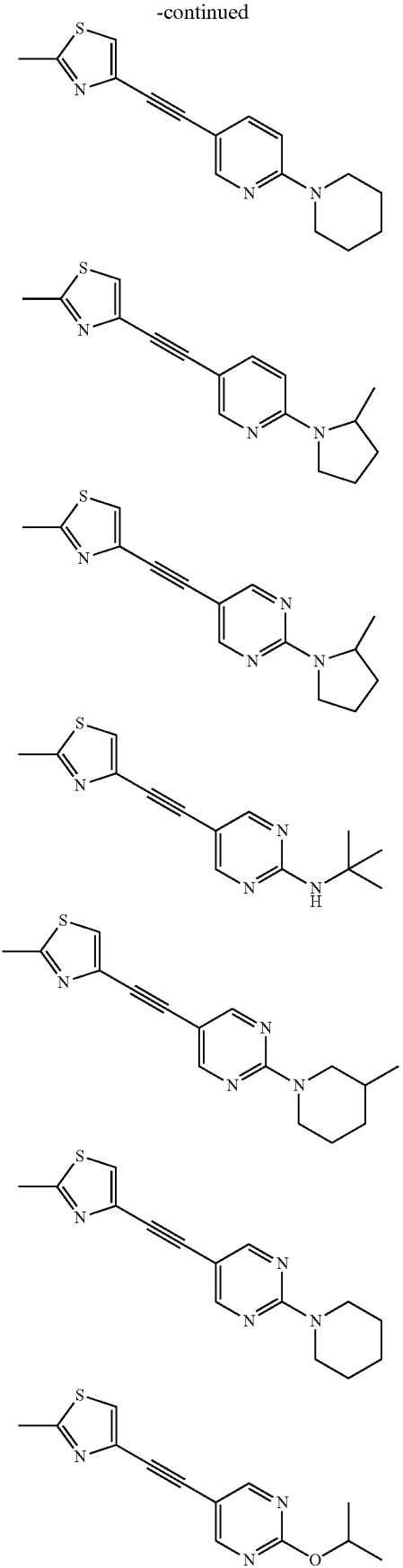
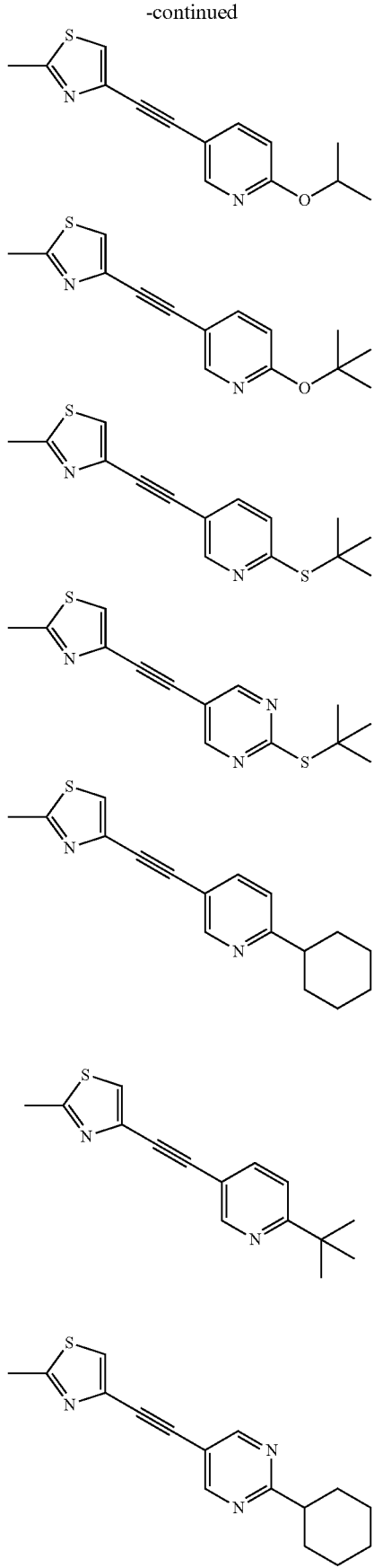

-continued
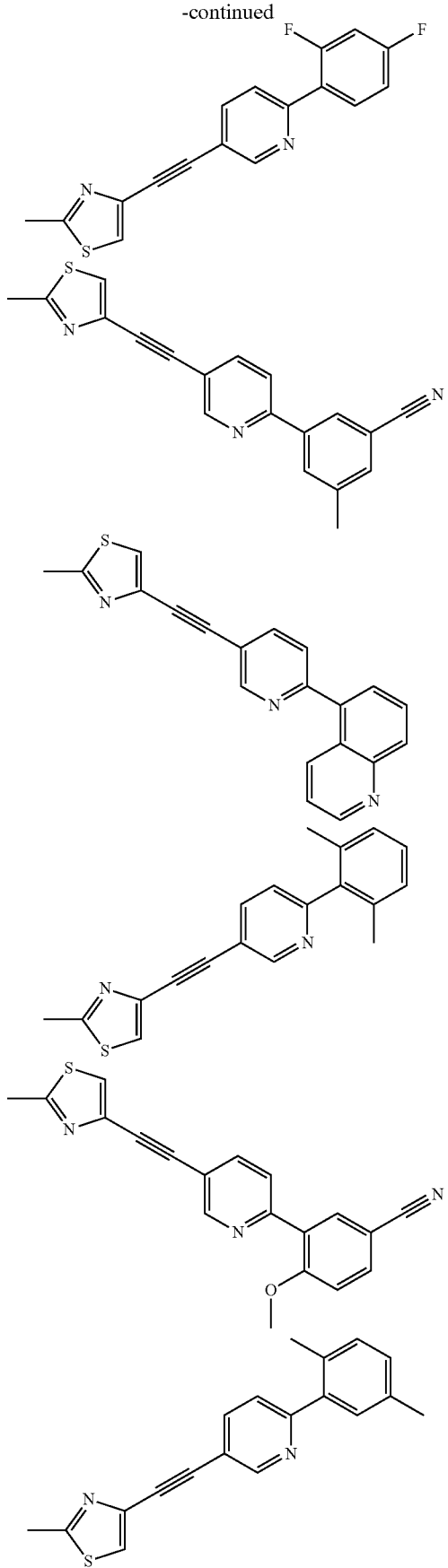
-continued
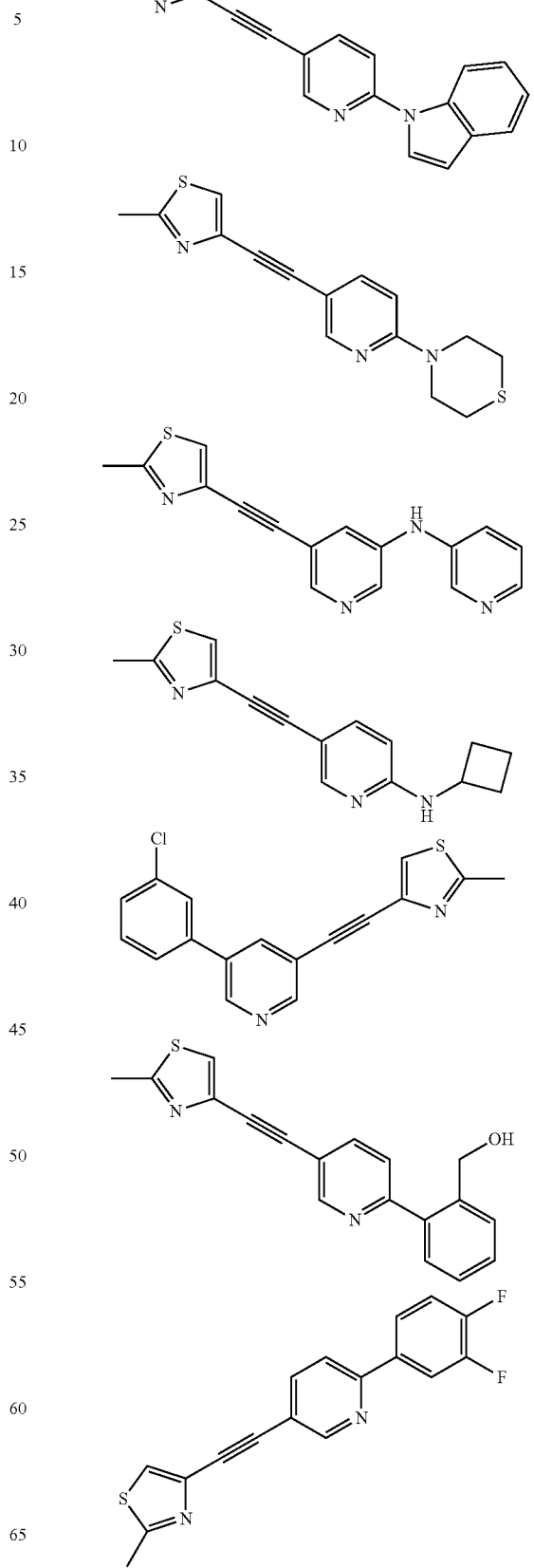

57
-continued
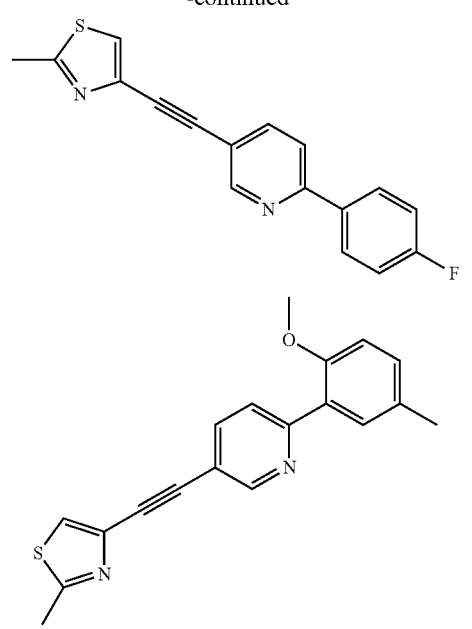
58
-continued
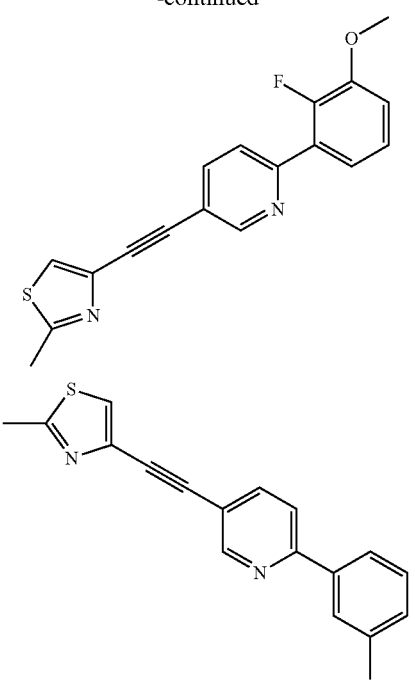
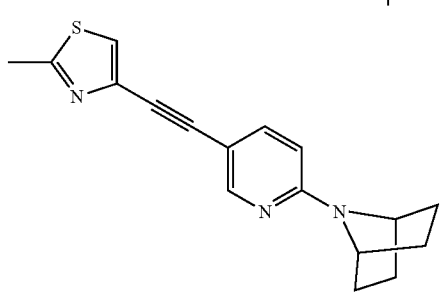
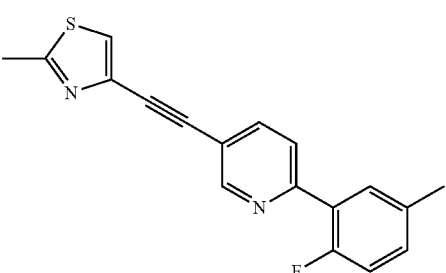
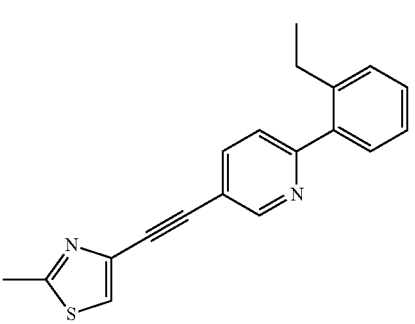

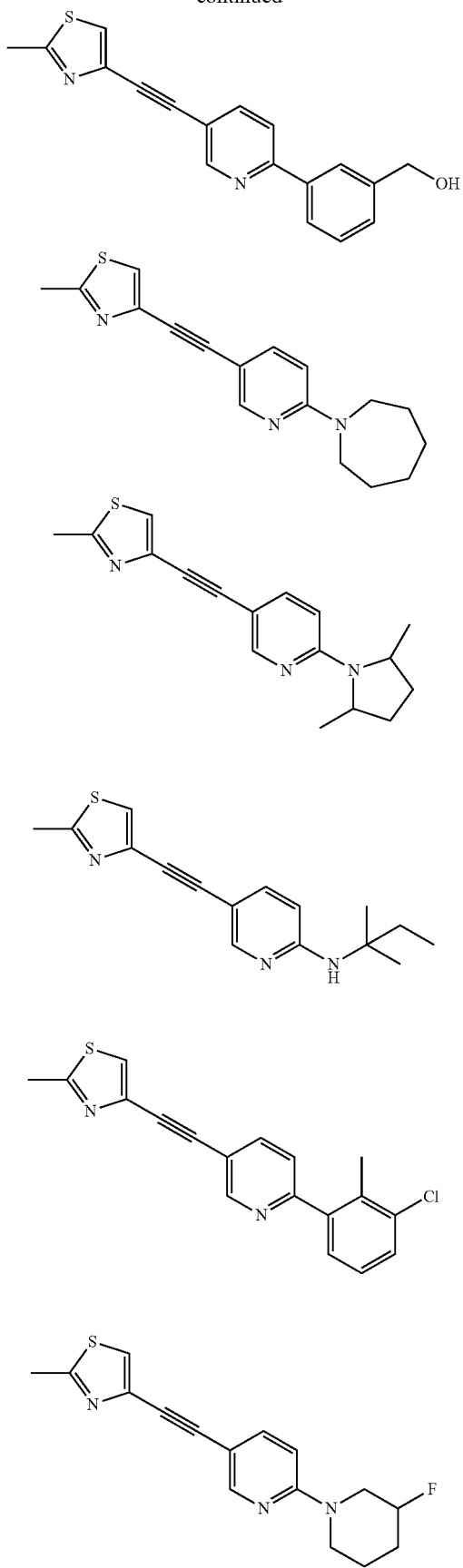
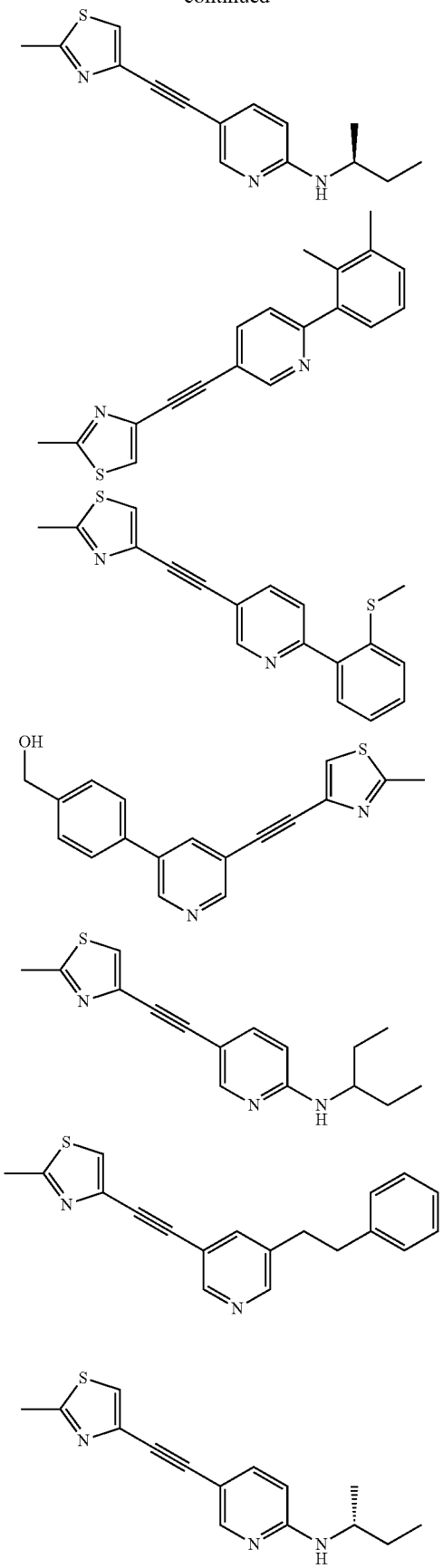

-continued
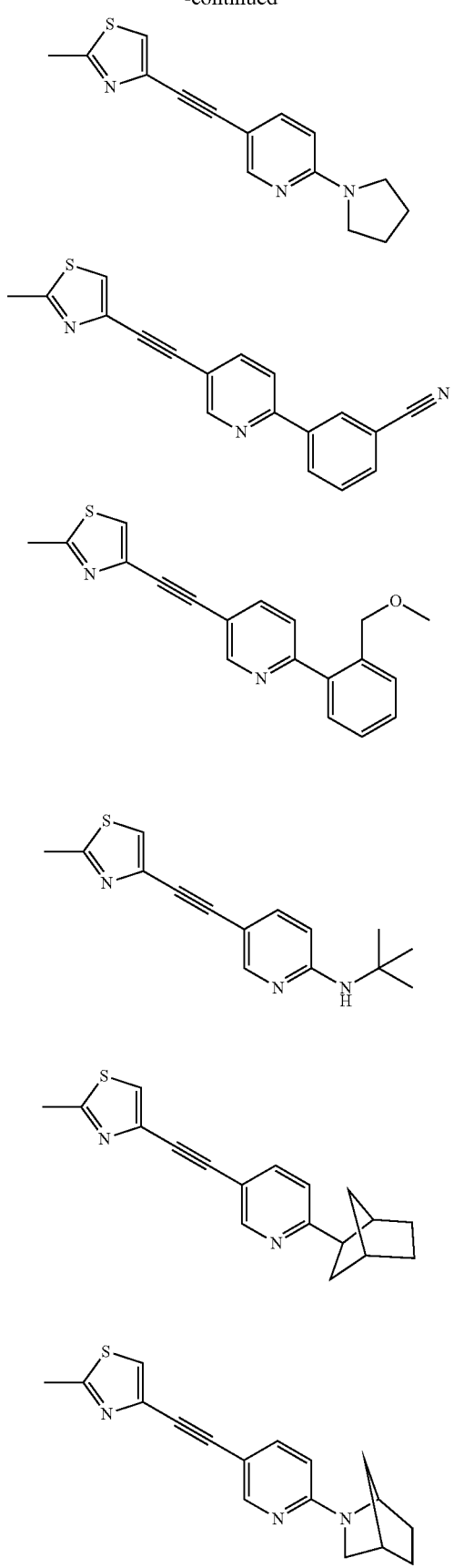
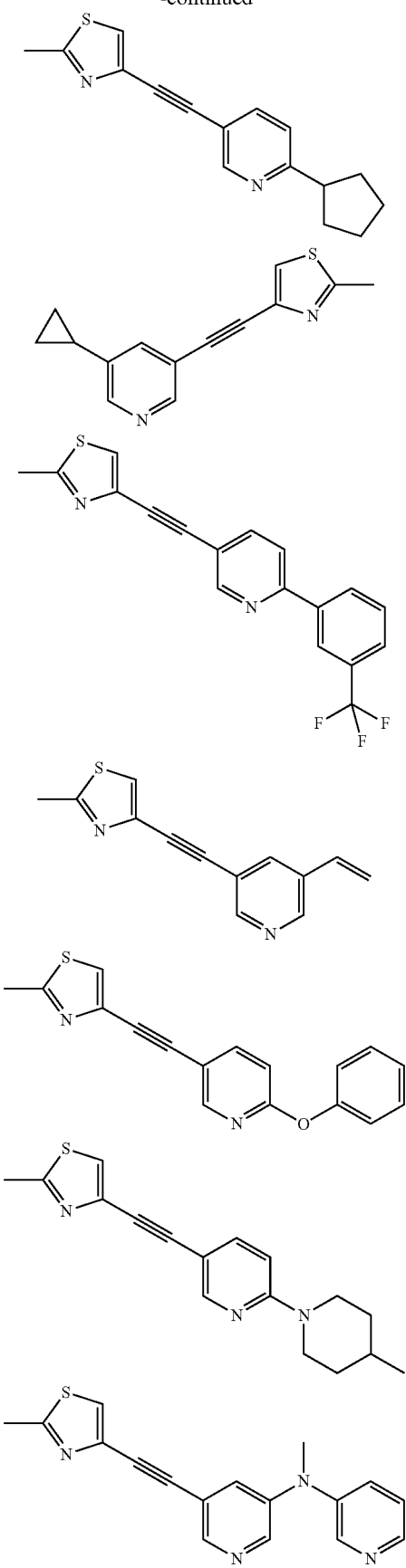

63
-continued
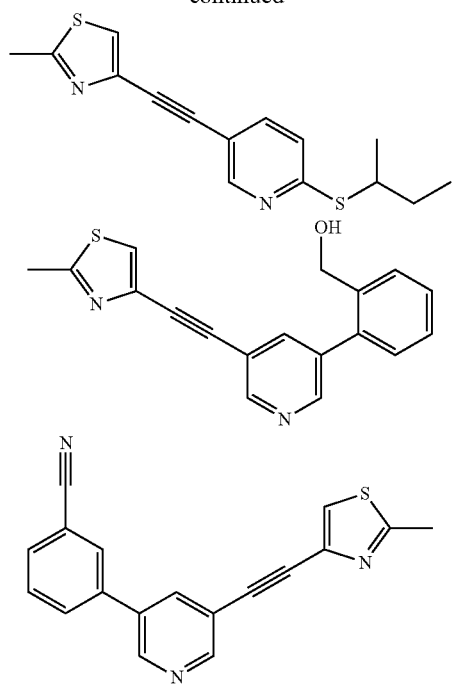
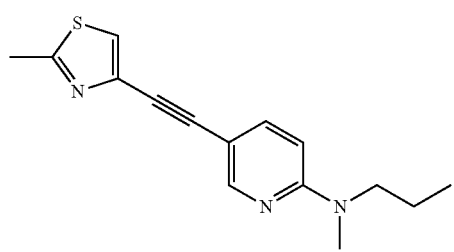
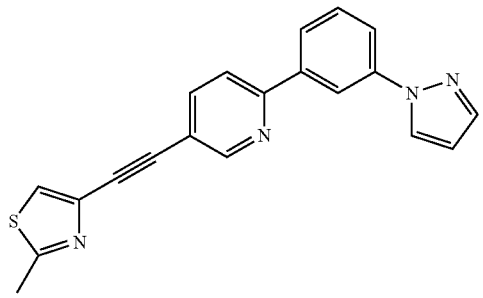
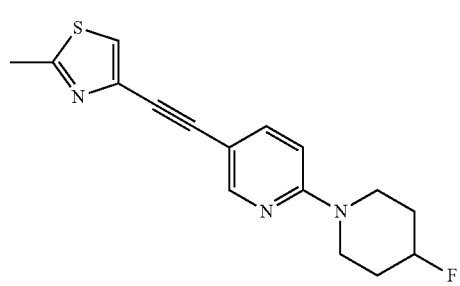
64
-continued
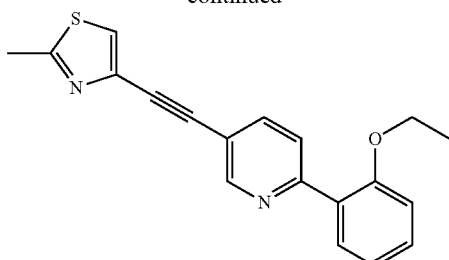
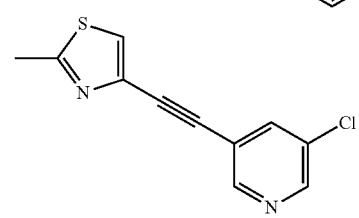
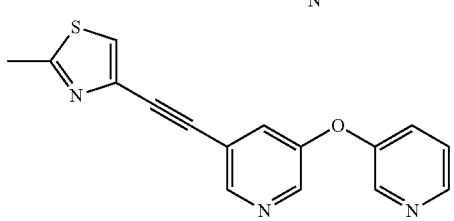
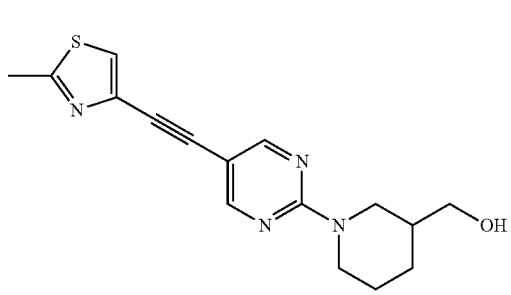
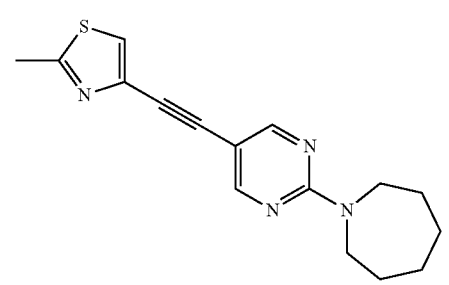
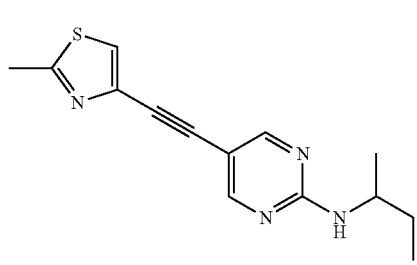

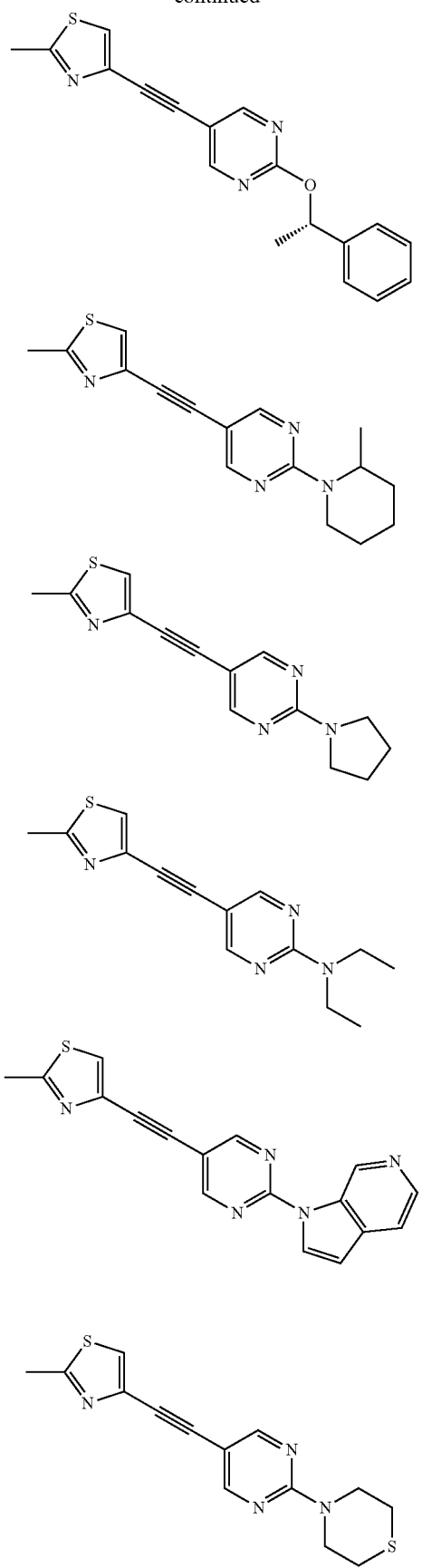
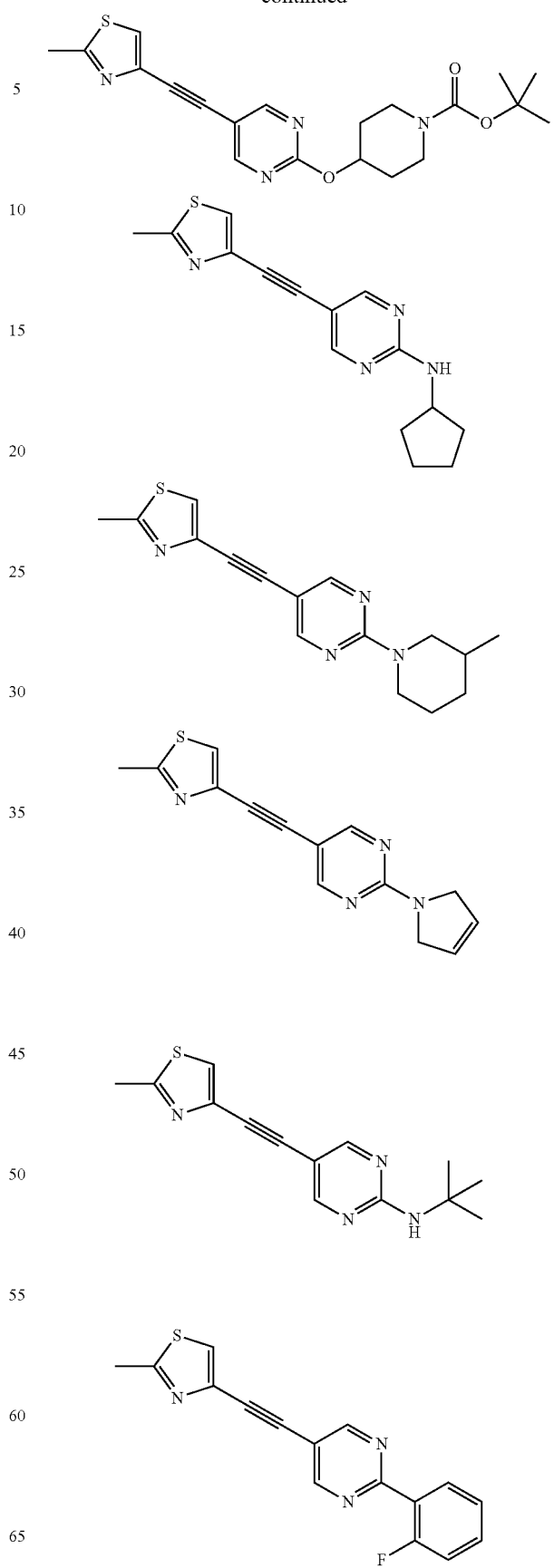

-continued
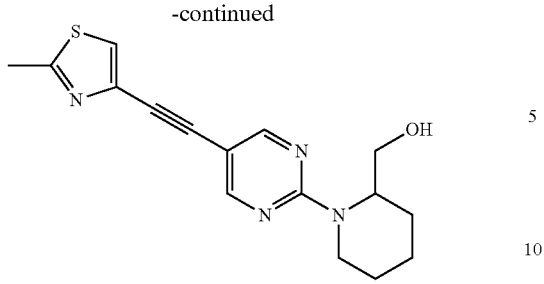
or a pharmaceutically acceptable salt thereof.
2. A pharmaceutical composition which comprises the compound of claim 1 or a pharmaceutically acceptable salt thereof and a pharmaceutically acceptable excipient.
* * * * *